United States Patent [19]

Suslow et al.

[11] Patent Number: 5,776,448
[45] Date of Patent: *Jul. 7, 1998

[54] CHITINASE-PRODUCING BACTERIA

[75] Inventors: Trevor V. Suslow, El Cerrito, Calif.;
Jonathan D.G. Jones, Norwich, United Kingdom

[73] Assignee: DNA Plant Technology Corporation, Oakland, Calif.

[*] Notice: The term of this patent shall not extend beyond the expiration date of Pat. No. 4,751,081.

[21] Appl. No.: 693,835

[22] Filed: Aug. 1, 1996

Related U.S. Application Data

[63] Continuation of Ser. No. 358,901, Dec. 19, 1994, Pat. No. 5,554,521, which is a continuation-in-part of Ser. No. 930,970, Aug. 14, 1992, Pat. No. 5,290,687, which is a continuation of Ser. No. 550,253, Jul. 9, 1990, Pat. No. 5,374,540, which is a continuation-in-part of Ser. No. 888,033, Jul. 18, 1986, Pat. No. 4,940,840, which is a continuation-in-part of Ser. No. 593,691, Mar. 26, 1984, Pat. No. 4,751,081.

[51] Int. Cl.$^6$ .............................. C12N 1/21; C12N 15/56; C12N 15/78; A01C 1/06; A61K 39/104
[52] U.S. Cl. .................. 424/93.2; 424/93.4; 424/93.47; 435/69.1; 435/71.1; 435/172.3; 435/209; 435/252.3; 435/252.33; 435/252.34; 47/57.6; 536/23.2; 536/23.7
[58] Field of Search ........................... 435/69.1, 71.1, 435/172.3, 209, 252.3, 252.34, 252.33; 424/93.2, 93.4, 93.47; 47/57.6; 536/23.2, 23.7

[56] References Cited

U.S. PATENT DOCUMENTS

| 4,751,081 | 6/1988 | Suslow et al. | 424/93 |
| 4,940,840 | 7/1990 | Suslow et al. | 800/205 |
| 5,290,687 | 3/1994 | Suslow et al. | 435/69.1 |
| 5,374,540 | 12/1994 | Suslow et al. | 435/69.8 |
| 5,378,821 | 1/1995 | Harman et al. | 536/23.2 |

FOREIGN PATENT DOCUMENTS

| 90/07001 | 6/1990 | WIPO | C12N 15/56 |
| 95J/05467 | 2/1995 | WIPO | C12N 15/56 |

OTHER PUBLICATIONS

Bevan and Chilton, "T-DNA of the agrobacterium TI and RI plasmids," *Ann. Rev. Genet.* 16 :357–384 (1982).
Bevan, "Binary agrobacterium vectors for plant transformation," *Nucleic Acids Research* 112:8711–8721 (1984).
Fraley et al., "Expression of bacterial genes in plant cells," *PNAS USA* 80:4803–4807 (1983).
Goodman et al., "Gene transfer in crop improvement," *Science* 236:48–54 (1987).
Herrera–Estrella et al., "Expression of Chimaeric genes transferred into plant cells using a TI–plasmid–derived vector," *Nature* 303:209–213 (1983).
Hoekema et al. "A binary plant vector strategy based on separation of Vir– and T–region of the *agrobacterium tumefaciens* TI –plasmid," *Nature* 303:179–180 (1983).

Horsch et al.; "Inheritance of functional foreign genes in plants, " *Science* 223:496–498 (1984).
Horwitz et al.; pp. 191–208 In: *Chitin, Chitesan and related enzymes*, Zikakis, J. (ed.), Academic Press, Orlando, Fl. (1984).
Jones et al., "High level expression of introduced chimaeric–genes in regenerated transformed plants," *EMBO J.* 4:2411–2418 (1985).
Jones et al.; "Isolation and characterization of genes encoding two Chitinase enzymes from serratia marcescens," *EMBO J.* 5(3) :467–473 (1986).
Jones et al., "Engineering bacterial chitinase genes for crop protection," *J. of Cellular Biochem.* Supp. 10C, Abstract J30, p. 15 (1986).
Kado and Lurquin, "Prospectus for genetic engineering in agriculture," Prospectus for Genetic Engineering in Agriculture, Chapter 14, *Phytopathogenic Prokaryotes* vol. 2, Mount and Lacy , eds., 303–325 (1982).
Lewin, R. "When does homology mean something else," *Science* 237:1570 (1979).
Marton et al., "In vitro transformation of cultured cells from *Nicotiana tabacum* by *Agrobacerium tumefaciens,* " *Nature* 27:129–131 (1979).
Michael and Nelson, "Antagonistic effect of soil bacteria on fusarium roseum 'culmorum ' from carnation," *Phytopathology* 62:1052–1056 (1972).
Mitchell and Alexander, "The mycolytic phenomenon and biological control of fusarium in soil," *Nature* 190:109–110 (1961).
Miller and Sands, "Effects of hydrolytic enzymes on plant––parasitic nematodes," *J. of Nematology* 9:192–197 (1977).
Monreal and Reese, "The chitinase of serratis marcescens," *Canadien J. of Microbiology* 15:689–696 (1969).
Odell et al., "Identification of DNA sequences required for activity of the cauliflower mosaic virus 35S promoter," *Nature* 313:810–812 (1985).
Ream and Gordon, "Crown gall disease and prospects for genetic manipulation of plants," *Science* 218:854–859 (1987).
Reeck et al., "'Homology 'in proteins and nucleic acids: terminology muddle and a way out of it," *Cell* 50:667 (1987).
Reid and Ogrydziak, "Chitinase–overproducing mutant of serratia marcescens," *Applied and Environmental Microbiology* 41:664–669 (1981).

(List continued on next page.)

*Primary Examiner*—David T. Fox
*Attorney, Agent, or Firm*—Townsend and Townsend and Crew LLP

[57] ABSTRACT

Novel bacterial strains are described which produce and secrete chitinase as a result of the introduction of foreign DNA linked to a sequence encoding chitinase, an enzyme that degrades chitin. The bacterial strains can be used to provide protection for plants against chitinase sensitive plant pathogens. Methods of preparing the chitinase producing bacterial cells are also described. Methods of protecting plants from chitinase sensitive pathogens are also described.

22 Claims, 4 Drawing Sheets

OTHER PUBLICATIONS

Roberts and Cabib, "Serratia marcescens chitinase: One-step purification and use for the determination of chitin," *Analytical Biochemistry* 127:204–412 (1982).

Sneh, "Use of rhizosphere chitinolytic bacteria for biological control," *Phytopath. Z.* 100:251–256 (1988).

Suslow et al., *Phytopathology* 78(12) Part 1:1556 (1988).

Van den Elzen et al., "Simple binary vectors for DNA transfer to plant cells," *Plant Molecular Biology* 5:149–154 (1985).

Broglie et al., "Transgenic plants with enhanced resistance to the fungal pathogen *Rhizoctonia solani*," *Science* 54:1194–1197 (1991).

Collinge et al., "Plant chitinase," *The Plant Journal* 3(1):31–40 (1993).

Howie et al., "Transgenic tobacco plants which express the chiA gene from *Serratia marcescens* have enhanced tolerance to *Rhizoctonia solani*,"*Transgenic Research* 3:90–98 (1984).

Lund et al., "A plant signal sequence enhances the secretion of bacterial ChiA in transgenic tobacco," *Plant Molecular Biology* 18:47–53 (1992).

Neuhaus et al., "High–level expression of a tobacco chitinase gene in *Nicotiana syvestris*. Susceptibility of transgenic plants to *Cercospora nicotianae* infection,"*Plant Molecular Biology* 16:141–151 (1991).

Roberts et al., "plant and bacterial chitinases differ in antiofungal activity," *Journal of General Microbiology* 134:169–176 (1988).

Sakai et al., "The role of sugar and related compounds in variations of freezing resistance," *Cryobiology* 5:160–174 (1968).

Sela–Buurlage et al., "only specific tobacco ( *Nicotiana tabacum* ) chitinases and $\beta$–1, 3–glucanases exhibit antifungal activity," *Plant Physiol.* 101:857–863 (1993).

Vierheilig et al., "Colonization of transgenic *Nicotiana sylvestris* plants, expressing different forms of *Nicotiana tabacum* chitinase, by the root pathogen *Rhizoctonia solani* and by the *Mycorrhizal symbiont glomus mosseae*," *MPMI* 6(2):261–264 (1993).

```
-360
CAG GGC GTT GTC AAT AAT GAC AAC ACC CTG GCT GAA GAG TGT GGT

GCA ATA CTG ATA AAT ATT TAT CTT TCC TTA ATA GAA AAT TCA CTA
-270
TCC TTA TTT GTC ATG TTT TCT TTT ATT TAT ATG AAA ATA AAT TCA

CGC TTG CTG AAT AAA ACC CAG TTG ATA GCG CTC TTG TTT TTG CGC
-180
CTT TTT TAT TTA TAG TAC TGA ATG TAC GCG GTG GGA ATG ATT ATT

TCG CCA CGT GGA AAG ACG CTG TTG TTA TTT ATT GAT TTT AAC CTT
-90
CGC GGA TTA TTG CGG AAT TTT TTC GCT TCG GCA ATG CAT CGC GAC

GAT TAA CTC TTT TAT GTT TAT CCT CTC GGA ATA AAG GAA TCA GTT
 1
MET ARG LYS PHE ASN LYS PRO LEU LEU ALA LEU LEU ILE GLY SER
ATG CGC AAA TTT AAT AAA CCG CTG TTG GCG CTG TTG ATC GGC AGC

THR LEU CYS SER ALA ALA GLN ALA ALA ALA PRO GLY LYS PRO THR
ACG CTG TGT TCC GCG GCG CAG GCC GCC GCG CCG GGC AAG CCG ACC
 91
ILE ALA TRP GLY ASN THR LYS PHE ALA ILE VAL GLU VAL ASP GLN
ATC GCC TGG GGC AAC ACC AAG TTC GCC ATC GTT GAA GTT GAC CAG

ALA ALA THR ALA TYR ASN ASN LEU VAL LYS VAL LYS ASN ALA ALA
GCG GCT ACC GCT TAT AAT AAT TTG GTG AAG GTA AAA AAT GCC GCC
181
ASP VAL SER VAL SER TRP ASN LEU TRP ASN GLY ASP ALA GLY THR
GAT GTT TCC GTC TCC TGG AAT TTA TGG AAT GGC GAC GCG GGC ACG

GLY PRO LYS ILE LEU LEU ASN GLY LYS GLU ALA TRP SER GLY PRO
GGA CCC AAG ATT TTA TTA AAT GGT AAA GAG GCG TGG AGT GGT CCT
-271
SER THR GLY SER SER GLY THR ALA ASN PHE LYS VAL ASN LYS GLY
TCA ACC GGA TCT TCC GGT ACG GCG AAT TTT AAA GTG AAT AAA GGC

GLY ARG TYR GLN MET GLN VAL ALA LEU CYS ASN ALA ASP GLY CYS
GGC CGT TAT CAA ATG CAG GTG GCA TTG TGC AAT GCC GAC GGC TGC
-361
THR ALA SER ASP ALA THR GLU ILE VAL VAL ALA ASP THR ASP GLY
ACC GCC AGT GAC GCC ACC GAA ATT GTG GTG GCC GAC ACC GAC GGC

SER HIS LEU PRO PRO LEU LYS GLU PRO LEU LEU GLU LYS ASN LYS
AGC CAT TTG CCG CCG TTG AAA GAG CCG CTG CTG GAA AAG AAT AAA
```

FIG. 1A.

```
451
PRO TYR LYS GLN ASN SER GLY LYS VAL VAL GLY SER TYR PHE VAL
CCG TAT AAA CAG AAC TCC GGC AAA GTG GTC GGT TCT TAT TTC GTC

GLU TRP GLY VAL TYR GLY ARG ASN PHE THR VAL ASP LYS ILE PRO
GAG TGG GGC GTT TAC GGG CGC AAT TTC ACC GTC GAC AAG ATC CCG

541
ALA GLN ASN LEU THR HIS LEU LEU TYR GLY PHE ILE PRO ILE CYS
GCG CAA AAC CTG ACC CAC CTG CTG TAC GGC TTT ATC CCG ATC TGC

GLY GLY ASN GLY ILE ASN ASP SER LEU LYS GLU ILE GLU GLY SER
GGC GGC AAT GGC ATC AAC GAC AGC CTG AAA GAG ATT GAA GGC AGC

631
PHE GLN ALA LEU GLN ARG SER CYS GLN GLY ARG GLU ASP PHE LYS
TTC CAG GCG TTG CAG CGC TCC TGC CAA GGC CGC GAG GAC TTC AAA

ILE SER ILE HIS ASP PRO PHE ALA ALA LEU GLN LYS ALA GLN LYS
ATC TCG ATC CAC GAT CCG TTC GCC GCG CTG CAA AAG GCG CAG AAG

721
GLY VAL THR ALA TRP ASP ASP PRO TYR LYS GLY ASN PHE GLY GLN
GGC GTG ACC GCC TGG GAT GAC CCC TAC AAG GGC AAC TTC GGC CAG

LEU MET ALA LEU LYS GLN ALA HIS PRO ASP LEU LYS ILE LEU PRO
CTG ATG GCG CTG AAG CAG GCG CAT CCT GAC CTG AAA ATC CTG CCG

811
SER ILE GLY GLY TRP THR LEU SER ASP PRO PHE PHE PHE MET GLY
TCG ATC GGC GGC TGG ACG CTG TCC GAC CCG TTC TTC TTC ATG GGC

ASP LYS VAL LYS ARG ASP ARG PHE VAL GLY SER VAL LYS GLU PHE
GAC AAG GTG AAG CGC GAT CGC TTC GTC GGT TCG GTG AAA GAG TTC

901
LEU GLN THR TRP LYS PHE PHE ASP GLY VAL ASP ILE ASP TRP GLU
CTG CAG ACC TGG AAG TTC TTC GAC GGC GTG GAT ATC GAC TGG GAG

PHE PRO GLY GLY LYS GLY ALA ASN PRO ASN LEU GLY SER PRO GLN
TTC CCG GGC GGC AAA GGC GCC AAC CCT AAC CTG GGC AGC CCG CAA

991
ASP GLY GLU THR TYR VAL LEU LEU MET LYS GLU LEU ARG ALA MET
GAC GGG GAA ACC TAT GTG CTG CTG ATG AAG GAG CTG CGG GCG ATG

LEU ASP GLN LEU SER ALA GLU THR GLY ARG LYS TYR GLU LEU THR
CTG GAT CAG CTG TCG GCG GAA ACC GGC CGC AAG TAT GAG CTG ACC

1081
SER ALA ILE SER ALA GLY LYS ASP LYS ILE ASP LYS VAL ALA TYR
TCC GCC ATC AGC GCC GGT AAG GAC AAG ATC GAC AAG GTG GCT TAC

ASN VAL ALA GLN ASN SER MET ASP HIS ILE PHE LEU MET SER TYR
AAC GTT GCG CAG AAC TCG ATG GAT CAC ATC TTC CTG ATG AGC TAC
```

FIG. 1B.

```
1171
ASP PHE TYR GLY ALA PHE ASP LEU LYS ASN LEU GLY HIS GLN THR
GAC TTC TAT GGC GCC TTC GAT CTG AAG AAC CTG GGG CAT CAG ACC

ALA LEU ASN ALA ARG PRO GLY SER ARG HIS ARG LEU HIS HIS GLY
GCG CTG AAT GCG CGG CCT GGA AGC CGA CAC CGC TTA CAC CAC GGT

1261
GLU ARG ARG GLU CYS ALA ALA GLY GLN GLY VAL LYS PRO GLY LYS
GAA CGG CGT GAA TGC GCT GCT GGC CAG GGC GTC AAG CCG GGC AAA

ILE VAL VAL GLY THR ALA MET TYR GLY ARG GLY TRP THR GLY VAL
ATC GTC GTC GGC ACC GCC ATG TAT GGC CGC GGC TGG ACC GGG GTG

1351
ASN GLY TYR GLN ASN ASN ILE PRO PHE THR GLY THR HIS ARG ALA
AAC GGC TAC CAG AAC AAC ATT CCG TTC ACC GGC ACG CAC CGG GCC

VAL LYS GLY THR TRP GLU ASN GLY ILE VAL ASP TYR ARG GLN ILE
GTT AAA GGC ACC TGG GAG AAC GGC ATC GTG GAC TAC CGC CAA ATC

1441
ALA SER GLN PHE MET SER GLY GLU TRP GLN TYR THR TYR ASP ALA
GCC AGC CAG TTC ATG AGC GGC GAG TGG CAG TAT ACC TAC GAC GCC

THR ALA GLU ALA PRO TYR VAL PHE LYS PRO SER THR GLY ASP LEU
ACG GCG GAG GCG CCT TAC GTG TTC AAA CCT TCC ACC GGC GAT CTG

1531
ILE THR PHE ASP ASP ALA ARG SER VAL GLY ALA LYS GLY LYS TYR
ATC ACC TCC GAC GAT GCC CGC TCG GTG CAG GCT AAA GGC AAG TAC

VAL LEU ASP LYS GLN LEU GLY GLY LEU PHE SER TRP GLU ILE ASP
GTG CTG GAT AAA CAG CTG GGC GGC CTG TTC TCC TGG GAG ATC GAC

1621
ALA ASP ASN GLY ASP ILE LEU ASN SER MET ASN ALA SER LEU GLY
GCG GAC AAC GGC GAT ATT CTC AAC AGC ATG AAC GCC AGC CTG GGC

ASN SER ALA GLY VAL GLN ***
AAC AGC GCC GGC GTT CAA TAA TCG GTT GCA GTG GTT GCC GGG GGA

1711
TAT CCT TTC GCC CCC GGC TTT TTC GCC GAC GAA AGT TTT TTT ACG

CCG CAC AGA TTG TGG CTC TGC CCC GAG CAA AAC GCG CTC ATC GGA

1801
CTC ACC CTT TTG GGT AAT CCT TCA GCA TTT CCT CCT GTC TTT AAC

GGC GAT CAC AAA AAT AAC CGT TCA GAT AAT CAT CAT TCA GCA ACA

1891
AAG TTT TGG CGT TTT TTA ACG GAG TTA AAA ACC AGT AAG TTT GTG

AGG GTC AGA CCA ATG CGC TAA AAA TGG G
```

*FIG. 1C.*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2323 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 361..2043

( x i ) SEQUENCE DESCRIPTION: SEQ ID NO:1:

```
CAGGGCGTTG TCAATAATGA CAACACCCTG GCTGAAGAGT GTGGTGCAAT ACTGATAAAT          60

ATTTATCTTT CCTTAATAGA AAATTCACTA TCCTTATTTG TCATGTTTTC TTTTATTTAT         120

ATGAAAATAA ATTCACGCTT GCTGAATAAA ACCCAGTTGA TAGCGCTCTT GTTTTGCGC          180

CTTTTTTATT TATAGTACTG AATGTACGCG GTGGGAATGA TTATTCGCC ACGTGGAAAG          240

ACGCTGTTGT TATTTATTGA TTTTAACCTT CGCGGATTAT TGCGGAATTT TTTCGCTTCG         300

GCAATGCATC GCGACGATTA ACTCTTTTAT GTTTATCCTC TCGGAATAAA GGAATCAGTT        360
```

| | | | | | | | | | | | | | | | | |
|---|---|---|---|---|---|---|---|---|---|---|---|---|---|---|---|---|
| ATG | CGC | AAA | TTT | AAT | AAA | CCG | CTG | TTG | GCG | CTG | TTG | ATC | GGC | AGC | ACG | 408 |
| Met | Arg | Lys | Phe | Asn | Lys | Pro | Leu | Leu | Ala | Leu | Leu | Ile | Gly | Ser | Thr | |
| 1 | | | | 5 | | | | | 10 | | | | | 15 | | |
| CTG | TGT | TCC | GCG | GCG | CAG | GCC | GCC | GCG | CCG | GGC | AAG | CCG | ACC | ATC | GCC | 456 |
| Leu | Cys | Ser | Ala | Ala | Gln | Ala | Ala | Ala | Pro | Gly | Lys | Pro | Thr | Ile | Ala | |
| | | | | 20 | | | | 25 | | | | | 30 | | | |
| TGG | GGC | AAC | ACC | AAG | TTC | GCC | ATC | GTT | GAA | GTT | GAC | CAG | GCG | GCT | ACC | 504 |
| Trp | Gly | Asn | Thr | Lys | Phe | Ala | Ile | Val | Glu | Val | Asp | Gln | Ala | Ala | Thr | |
| | | 35 | | | | | 40 | | | | | 45 | | | | |
| GCT | TAT | AAT | AAT | TTG | GTG | AAG | GTA | AAA | AAT | GCC | GCC | GAT | GTT | TCC | GTC | 552 |
| Ala | Tyr | Asn | Asn | Leu | Val | Lys | Val | Lys | Asn | Ala | Ala | Asp | Val | Ser | Val | |
| | 50 | | | | | 55 | | | | | 60 | | | | | |
| TCC | TGG | AAT | TTA | TGG | AAT | GGC | GAC | GCG | GGC | ACG | GGA | CCC | AAG | ATT | TTA | 600 |
| Ser | Trp | Asn | Leu | Trp | Asn | Gly | Asp | Ala | Gly | Thr | Gly | Pro | Lys | Ile | Leu | |
| 65 | | | | | 70 | | | | | 75 | | | | | 80 | |
| TTA | AAT | GGT | AAA | GAG | GCG | TGG | AGT | GGT | CCT | TCA | ACC | GGA | TCT | TCC | GGT | 648 |
| Leu | Asn | Gly | Lys | Glu | Ala | Trp | Ser | Gly | Pro | Ser | Thr | Gly | Ser | Ser | Gly | |
| | | | | 85 | | | | | 90 | | | | | 95 | | |
| ACG | GCG | AAT | TTT | AAA | GTG | AAT | AAA | GGC | GGC | CGT | TAT | CAA | ATG | CAG | GTG | 696 |
| Thr | Ala | Asn | Phe | Lys | Val | Asn | Lys | Gly | Gly | Arg | Tyr | Gln | Met | Gln | Val | |
| | | | | 100 | | | | | 105 | | | | | 110 | | |
| GCA | TTG | TGC | AAT | GCC | GAC | GGC | TGC | ACC | GCC | AGT | GAC | GCC | ACC | GAA | ATT | 744 |
| Ala | Leu | Cys | Asn | Ala | Asp | Gly | Cys | Thr | Ala | Ser | Asp | Ala | Thr | Glu | Ile | |
| | | 115 | | | | | 120 | | | | | 125 | | | | |
| GTG | GTG | GCC | GAC | ACC | GAC | GGC | AGC | CAT | TTG | CCG | CCG | TTG | AAA | GAG | CCG | 792 |
| Val | Val | Ala | Asp | Thr | Asp | Gly | Ser | His | Leu | Pro | Pro | Leu | Lys | Glu | Pro | |
| | 130 | | | | | 135 | | | | | 140 | | | | | |
| CTG | CTG | GAA | AAG | AAT | AAA | CCG | TAT | AAA | CAG | AAC | TCC | GGC | AAA | GTG | GTC | 840 |
| Leu | Leu | Glu | Lys | Asn | Lys | Pro | Tyr | Lys | Gln | Asn | Ser | Gly | Lys | Val | Val | |
| 145 | | | | | 150 | | | | | 155 | | | | | 160 | |
| GGT | TCT | TAT | TTC | GTC | GAG | TGG | GGC | GTT | TAC | GGG | CGC | AAT | TTC | ACC | GTC | 888 |
| Gly | Ser | Tyr | Phe | Val | Glu | Trp | Gly | Val | Tyr | Gly | Arg | Asn | Phe | Thr | Val | |
| | | | | 165 | | | | | 170 | | | | | 175 | | |
| GAC | AAG | ATC | CCG | GCG | CAA | AAC | CTG | ACC | CAC | CTG | CTG | TAC | GGC | TTT | ATC | 936 |
| Asp | Lys | Ile | Pro | Ala | Gln | Asn | Leu | Thr | His | Leu | Leu | Tyr | Gly | Phe | Ile | |
| | | | 180 | | | | | 185 | | | | | 190 | | | |
| CCG | ATC | TGC | GGC | GGC | AAT | GGC | ATC | AAC | GAC | AGC | CTG | AAA | GAG | ATT | GAA | 984 |
| Pro | Ile | Cys | Gly | Gly | Asn | Gly | Ile | Asn | Asp | Ser | Leu | Lys | Glu | Ile | Glu | |
| | | 195 | | | | | 200 | | | | | 205 | | | | |
| GGC | AGC | TTC | CAG | GCG | TTG | CAG | CGC | TCC | TGC | CAA | GGC | CGC | GAG | GAC | TTC | 1032 |
| Gly | Ser | Phe | Gln | Ala | Leu | Gln | Arg | Ser | Cys | Gln | Gly | Arg | Glu | Asp | Phe | |
| | | 210 | | | | | 215 | | | | | 220 | | | | |
| AAA | ATC | TCG | ATC | CAC | GAT | CCG | TTC | GCC | GCG | CTG | CAA | AAG | GCG | CAG | AAG | 1080 |
| Lys | Ile | Ser | Ile | His | Asp | Pro | Phe | Ala | Ala | Leu | Gln | Lys | Ala | Gln | Lys | |
| 225 | | | | | 230 | | | | | 235 | | | | | 240 | |
| GGC | GTG | ACC | GCC | TGG | GAT | GAC | CCC | TAC | AAG | GGC | AAC | TTC | GGC | CAG | CTG | 1128 |
| Gly | Val | Thr | Ala | Trp | Asp | Asp | Pro | Tyr | Lys | Gly | Asn | Phe | Gly | Gln | Leu | |
| | | | | 245 | | | | | 250 | | | | | 255 | | |
| ATG | GCG | CTG | AAG | CAG | GCG | CAT | CCT | GAC | CTG | AAA | ATC | CTG | CCG | TCG | ATC | 1176 |
| Met | Ala | Leu | Lys | Gln | Ala | His | Pro | Asp | Leu | Lys | Ile | Leu | Pro | Ser | Ile | |
| | | | 260 | | | | | 265 | | | | | 270 | | | |

-continued

```
GGC GGC TGG ACG CTG TCC GAC CCG TTC TTC TTC ATG GGC GAC AAG GTG         1224
Gly Gly Trp Thr Leu Ser Asp Pro Phe Phe Phe Met Gly Asp Lys Val
        275                 280                 285

AAG CGC GAT CGC TTC GTC GGT TCG GTG AAA GAG TTC CTG CAG ACC TGG         1272
Lys Arg Asp Arg Phe Val Gly Ser Val Lys Glu Phe Leu Gln Thr Trp
        290                 295                 300

AAG TTC TTC GAC GGC GTG GAT ATC GAC TGG GAG TTC CCG GGC GGC AAA         1320
Lys Phe Phe Asp Gly Val Asp Ile Asp Trp Glu Phe Pro Gly Gly Lys
305                 310                 315                 320

GGC GCC AAC CCT AAC CTG GGC AGC CCG CAA GAC GGG GAA ACC TAT GTG         1368
Gly Ala Asn Pro Asn Leu Gly Ser Pro Gln Asp Gly Glu Thr Tyr Val
                325                 330                 335

CTG CTG ATG AAG GAG CTG CGG GCG ATG CTG GAT CAG CTG TCG GCG GAA         1416
Leu Leu Met Lys Glu Leu Arg Ala Met Leu Asp Gln Leu Ser Ala Glu
                340                 345                 350

ACC GGC CGC AAG TAT GAG CTG ACC TCC GCC ATC AGC GCC GGT AAG GAC         1464
Thr Gly Arg Lys Tyr Glu Leu Thr Ser Ala Ile Ser Ala Gly Lys Asp
                355                 360                 365

AAG ATC GAC AAG GTG GCT TAC AAC GTT GCG CAG AAC TCG ATG GAT CAC         1512
Lys Ile Asp Lys Val Ala Tyr Asn Val Ala Gln Asn Ser Met Asp His
        370                 375                 380

ATC TTC CTG ATG AGC TAC GAC TTC TAT GGC GCC TTC GAT CTG AAG AAC         1560
Ile Phe Leu Met Ser Tyr Asp Phe Tyr Gly Ala Phe Asp Leu Lys Asn
385                 390                 395                 400

CTG GGG CAT CAG ACC GCG CTG AAT GCG CGG CCT GGA AGC CGA CAC CGC         1608
Leu Gly His Gln Thr Ala Leu Asn Ala Arg Pro Gly Ser Arg His Arg
                405                 410                 415

TTA CAC CAC GGT GAA CGG CGT GAA TGC GCT GCT GGC CAG GGC GTC AAG         1656
Leu His His Gly Glu Arg Arg Glu Cys Ala Ala Gly Gln Gly Val Lys
                420                 425                 430

CCG GGC AAA ATC GTC GTC GGC ACC GCC ATG TAT GGC CGC GGC TGG ACC         1704
Pro Gly Lys Ile Val Val Gly Thr Ala Met Tyr Gly Arg Gly Trp Thr
        435                 440                 445

GGG GTG AAC GGC TAC CAG AAC AAC ATT CCG TTC ACC GGC ACG CAC CGG         1752
Gly Val Asn Gly Tyr Gln Asn Asn Ile Pro Phe Thr Gly Thr His Arg
        450                 455                 460

GCC GTT AAA GGC ACC TGG GAG AAC GGC ATC GTG GAC TAC CGC CAA ATC         1800
Ala Val Lys Gly Thr Trp Glu Asn Gly Ile Val Asp Tyr Arg Gln Ile
465                 470                 475                 480

GCC AGC CAG TTC ATG AGC GGC GAG TGG CAG TAT ACC TAC GAC GCC ACG         1848
Ala Ser Gln Phe Met Ser Gly Glu Trp Gln Tyr Thr Tyr Asp Ala Thr
                485                 490                 495

GCG GAG GCG CCT TAC GTG TTC AAA CCT TCC ACC GGC GAT CTG ATC ACC         1896
Ala Glu Ala Pro Tyr Val Phe Lys Pro Ser Thr Gly Asp Leu Ile Thr
                500                 505                 510

TCC GAC GAT GCC CGC TCG GTG CAG GCT AAA GGC AAG TAC GTG CTG GAT         1944
Ser Asp Asp Ala Arg Ser Val Gln Ala Lys Gly Lys Tyr Val Leu Asp
        515                 520                 525

AAA CAG CTG GGC GGC CTG TTC TCC TGG GAG ATC GAC GCG GAC AAC GGC         1992
Lys Gln Leu Gly Gly Leu Phe Ser Trp Glu Ile Asp Ala Asp Asn Gly
530                 535                 540

GAT ATT CTC AAC AGC ATG AAC GCC AGC CTG GGC AAC AGC GCC GGC GTT         2040
Asp Ile Leu Asn Ser Met Asn Ala Ser Leu Gly Asn Ser Ala Gly Val
545                 550                 555                 560

CAA TAATCGGTTG CAGTGGTTGC CGGGGGATAT CCTTTCGCCC CCGGCTTTTT             2093
Gln

CGCCGACGAA AGTTTTTTTA CGCCGCACAG ATTGTGGCTC TGCCCCGAGC AAAACGCGCT      2153

CATCGGACTC ACCCTTTTGG GTAATCCTTC AGCATTTCCT CCTGTCTTTA ACGGCGATCA      2213
```

-continued

```
CAAAAATAAC CGTTCAGATA ATCATCATTC AGCAACAAAG TTTTGGCGTT TTTTAACGGA        2273
GTTAAAAACC AGTAAGTTTG TGAGGGTCAG ACCAATGCGC TAAAAATGGG                   2323
```

( 2 ) INFORMATION FOR SEQ ID NO:2:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Lys  Phe  Asn  Lys  Pro  Leu  Leu  Ala  Leu  Leu  Ile  Gly  Ser  Thr
 1              5                        10                       15

Leu  Cys  Ser  Ala  Ala  Gln  Ala  Ala  Ala  Pro  Gly  Lys  Pro  Thr  Ile  Ala
              20                       25                       30

Trp  Gly  Asn  Thr  Lys  Phe  Ala  Ile  Val  Glu  Val  Asp  Gln  Ala  Ala  Thr
              35                       40                       45

Ala  Tyr  Asn  Asn  Leu  Val  Lys  Val  Lys  Asn  Ala  Ala  Asp  Val  Ser  Val
         50                       55                       60

Ser  Trp  Asn  Leu  Trp  Asn  Gly  Asp  Ala  Gly  Thr  Gly  Pro  Lys  Ile  Leu
 65                       70                       75                       80

Leu  Asn  Gly  Lys  Glu  Ala  Trp  Ser  Gly  Ser  Thr  Gly  Ser  Ser  Gly
              85                       90                            95

Thr  Ala  Asn  Phe  Lys  Val  Asn  Lys  Gly  Gly  Arg  Tyr  Gln  Met  Gln  Val
                  100                      105                 110

Ala  Leu  Cys  Asn  Ala  Asp  Gly  Cys  Thr  Ala  Ser  Asp  Ala  Thr  Glu  Ile
              115                      120                 125

Val  Val  Ala  Asp  Thr  Asp  Gly  Ser  His  Leu  Pro  Pro  Leu  Lys  Glu  Pro
 130                      135                      140

Leu  Leu  Glu  Lys  Asn  Lys  Pro  Tyr  Lys  Gln  Asn  Ser  Gly  Lys  Val  Val
 145                      150                      155                 160

Gly  Ser  Tyr  Phe  Val  Glu  Trp  Gly  Val  Tyr  Gly  Arg  Asn  Phe  Thr  Val
                  165                      170                      175

Asp  Lys  Ile  Pro  Ala  Gln  Asn  Leu  Thr  His  Leu  Leu  Tyr  Gly  Phe  Ile
                  180                      185                 190

Pro  Ile  Cys  Gly  Gly  Asn  Gly  Ile  Asn  Asp  Ser  Leu  Lys  Glu  Ile  Glu
              195                      200                 205

Gly  Ser  Phe  Gln  Ala  Leu  Gln  Arg  Ser  Cys  Gln  Gly  Arg  Glu  Asp  Phe
         210                      215                 220

Lys  Ile  Ser  Ile  His  Asp  Pro  Phe  Ala  Ala  Leu  Gln  Lys  Ala  Gln  Lys
 225                      230                      235                 240

Gly  Val  Thr  Ala  Trp  Asp  Asp  Pro  Tyr  Lys  Gly  Asn  Phe  Gly  Gln  Leu
                  245                      250                 255

Met  Ala  Leu  Lys  Gln  Ala  His  Pro  Asp  Leu  Lys  Ile  Leu  Pro  Ser  Ile
              260                      265                 270

Gly  Gly  Trp  Thr  Leu  Ser  Asp  Pro  Phe  Phe  Phe  Met  Gly  Asp  Lys  Val
         275                      280                 285

Lys  Arg  Asp  Arg  Phe  Val  Gly  Ser  Val  Lys  Glu  Phe  Leu  Gln  Thr  Trp
 290                      295                 300

Lys  Phe  Phe  Asp  Gly  Val  Asp  Ile  Asp  Trp  Glu  Phe  Pro  Gly  Gly  Lys
 305                      310                 315                      320

Gly  Ala  Asn  Pro  Asn  Leu  Gly  Ser  Pro  Gln  Asp  Gly  Glu  Thr  Tyr  Val
                  325                      330                      335

Leu  Leu  Met  Lys  Glu  Leu  Arg  Ala  Met  Leu  Asp  Gln  Leu  Ser  Ala  Glu
```

|   |   |   |   |   |   |   | 340 |   |   |   |   | 345 |   |   |   |   | 350 |   |   |
|---|---|---|---|---|---|---|---|---|---|---|---|---|---|---|---|---|---|---|---|
| Thr | Gly | Arg 355 | Lys | Tyr | Glu | Leu | Thr 360 | Ser | Ala | Ile | Ser | Ala 365 | Gly | Lys | Asp |
| Lys | Ile 370 | Asp | Lys | Val | Ala | Tyr 375 | Asn | Val | Ala | Gln | Asn 380 | Ser | Met | Asp | His |
| Ile 385 | Phe | Leu | Met | Ser | Tyr 390 | Asp | Phe | Tyr | Gly | Ala 395 | Phe | Asp | Leu | Lys | Asn 400 |
| Leu | Gly | His | Gln | Thr 405 | Ala | Leu | Asn | Ala | Arg 410 | Pro | Gly | Ser | Arg | His 415 | Arg |
| Leu | His | His | Gly 420 | Glu | Arg | Arg | Glu | Cys 425 | Ala | Ala | Gly | Gln | Gly 430 | Val | Lys |
| Pro | Gly | Lys 435 | Ile | Val | Val | Gly | Thr 440 | Ala | Met | Tyr | Gly | Arg 445 | Gly | Trp | Thr |
| Gly | Val 450 | Asn | Gly | Tyr | Gln | Asn 455 | Asn | Ile | Pro | Phe | Thr 460 | Gly | Thr | His | Arg |
| Ala 465 | Val | Lys | Gly | Thr | Trp 470 | Glu | Asn | Gly | Ile | Val 475 | Asp | Tyr | Arg | Gln | Ile 480 |
| Ala | Ser | Gln | Phe | Met 485 | Ser | Gly | Glu | Trp | Gln 490 | Tyr | Thr | Tyr | Asp | Ala 495 | Thr |
| Ala | Glu | Ala | Pro 500 | Tyr | Val | Phe | Lys | Pro 505 | Ser | Thr | Gly | Asp | Leu 510 | Ile | Thr |
| Ser | Asp | Asp 515 | Ala | Arg | Ser | Val | Gln 520 | Ala | Lys | Gly | Lys | Tyr 525 | Val | Leu | Asp |
| Lys | Gln 530 | Leu | Gly | Gly | Leu | Phe 535 | Ser | Trp | Glu | Ile | Asp 540 | Ala | Asp | Asn | Gly |
| Asp 545 | Ile | Leu | Asn | Ser | Met 550 | Asn | Ala | Ser | Leu | Gly 555 | Asn | Ser | Ala | Gly | Val 560 |
| Gln |   |   |   |   |   |   |   |   |   |   |   |   |   |   |   |

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:3:

GGAATCAGTT ATGCGC        16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:4:

GGAATCACAT ATGCGC        16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single ( D ) TOPOLOGY: linear ( i i ) MOLECULE TYPE: DNA (oligonucleotide)

( x i ) SEQUENCE DESCRIPTION: SEQ ID NO:5:

TCTGCATATG CGCAAA                                                                16

( 2 ) INFORMATION FOR SEQ ID NO:6:

( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (oligonucleotide)

( x i ) SEQUENCE DESCRIPTION: SEQ ID NO:6:

TCTGAATATG CGCAAA                                                                16

( 2 ) INFORMATION FOR SEQ ID NO:7:

( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (oligonucleotide)

( x i ) SEQUENCE DESCRIPTION: SEQ ID NO:7:

TCTGAATATG GCCAAA                                                                16

( 2 ) INFORMATION FOR SEQ ID NO:8:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: DNA (oligonucleotide)

( x i ) SEQUENCE DESCRIPTION: SEQ ID NO:8:

AAACCATGGC CAGATCCCGG G                                                          21

( 2 ) INFORMATION FOR SEQ ID NO:9:

( i ) SEQUENCE CHARACTERISTICS:
              ( A ) LENGTH: 14 base pairs
              ( B ) TYPE: nucleic acid
              ( C ) STRANDEDNESS: single
              ( D ) TOPOLOGY: linear ( i i ) MOLECULE TYPE: DNA (oligonucleotide)

( x i ) SEQUENCE DESCRIPTION: SEQ ID NO:9:

AAACCATGGC CAAA                                                                  14

( 2 ) INFORMATION FOR SEQ ID NO:10:

( i ) SEQUENCE CHARACTERISTICS:
              ( A ) LENGTH: 14 base pairs
              ( B ) TYPE: nucleic acid
              ( C ) STRANDEDNESS: single
              ( D ) TOPOLOGY: linear -continued ( i i ) MOLECULE TYPE: DNA (oligonucleotide)

( x i ) SEQUENCE DESCRIPTION: SEQ ID NO:10:

TAACCATGGC CAAA 14

CHITINASE-PRODUCING BACTERIA

This application is a continuation of application Ser. No. 08/358,901, filed Dec. 19, 1994, which issued as Pat. No. 5,554,521, which is a continuation-in-part of application Ser. No. 07/930,970, filed Aug. 14, 1992, which issued as Pat. No. 5,290,687, which is a continuation of application Ser. No. 07/550,253, filed Jul. 9, 1990, which issued as Pat. No. 5,374,540, which is a continuation-in-part of application Ser. No. 06/888,033, filed Jul. 18, 1986, which issued as Pat. No. 4,940,840, which is a continuation-in-part of application Ser. No. 06/593,691, filed Mar. 26, 1984, which issued as Pat. No. 4,751,081, all in the names of Trevor V. Suslow and Jonathan D. G. Jones. All of the above are incorporated herein by reference.

This invention was made in part with Government support under Grant Nos. 9400067 and 94-33610-139 awarded by the United States Department of Agriculture. The Government has certain rights in this invention.

BACKGROUND OF THE INVENTION

This invention relates to novel man-made bacterial strains which produce chitinase, an enzyme which degrades chitin. This invention further relates to the use of such strains as a means to inhibit soil fungi and nematodes and to enhance plant growth by biological control of plant pathogens. This invention additionally relates to the introduction of chitinase activity into plants and to plants which have been rendered resistant to plant pathogens as a result of such introduction, and to plants which have been rendered resistant to chilling or frost (freezing) damage as a result of such introduction. Finally, this invention relates to the introduction into plant cells of a sequence from the chitinase gene that directs the secretion of polypeptides encoded by foreign DNA.

The soil contains a wide variety of life forms which can interact with plants, including bacteria, fungi and nematodes. These life forms are especially abundant in the rhizosphere, the area of the soil that surrounds and is influenced by the plant roots. As used herein the term rhizosphere embraces the rhizoplane, the root-soil interface including the surface of the root. The term rhizobacteria, as used herein, refers to bacteria adapted to the rhizosphere. The interactions between these soil inhabiting life forms are complex, some being antagonistic and others being mutually beneficial.

The interactions between plants and the various soil life forms are similarly complex, in some instances helpful to the plant and in other instances deleterious to the plant. Fungi harmful to plants (fungal pathogens) include fungal species from a wide variety of genera, including Fusarium, Pythium, Phytophthora, Verticillium, Rhizoctonia, Macrophomina, Thielaviopsis, Sclerotinia and numerous others. Plant diseases caused by fungi include pre and post-emergence seedling damping-off, hypocotyl rots, root rots, crown rots, vascular wilts and a variety of other forms of symptom development. Nematodes harmful to plants (nematode pathogens) include nematode species from the genera Meloidogyne, Heterodera, Ditylenchus, Pratylenchus. Plant diseases caused by nematodes include root galls, root rot, lesions, "stubby" root, stunting, and various other rots and wilts associated with increased infection by pathogenic fungi. Some nematodes (e.g., Trichodorus, Lonaidorus, Xiphenema) can serve as vectors for virus diseases in a number of plants including Prunus, grape, tobacco and tomato.

Various approaches are available for attempting to control deleterious fungi and nematodes. One method, long known in the art, is chemical treatment of soil or plants with fungicides or nematicides. Another method is application of certain naturally occurring bacteria which inhibit or interfere with fungi or nematodes. See, in general, K. F. Baker and R. J. Cook, Biological Control of Plant Pathogens, Freeman and Co. (1974) for a description of fungi and nematodes and their interaction with plants, as well as a description of means for biological control of fungal and nematode pathogens.

One approach to biocontrol of fungal and nematode pathogens is based on the widespread presence of chitin as an integral part of the cell walls of fungi and the outer covering of nematodes or nematode eggs or nematode cysts. Chitin is an unbranched polysaccharide polymer consisting of N-acetyl-D-glucosamine units ("GluNAc") joined by beta-1,4 glycosidic linkages. Chitin is insoluble in water, dilute mineral acids and bases but can be broken down enzymatically by chitinase, the degradation products being soluble monomers or multimers of GluNAc. Chitinases are a class of hydrolytic enzymes which degrade chitin by endolytic or exolytic mechanisms. The endochitinases, e.g., many of the chitinases found in plants, cleave the internal beta-1,4 glycosidic linkages in the chitin molecules to liberate oligomers of at least 3 GluNAc units. The exochitinases, e.g., bacterial chitinases such as present in Serratia marcescens hydrolyze beta-1,4 glycosidic bonds and release GluNAc; see Roberts et al., "Plant and Bacterial Chitinases Differ in Antifungal Activity", (1988) J. Gen. Microbiol. 134, 169–176, and references cited therein. Chitinase is produced by certain naturally occurring bacteria, fungi, nematodes, insects, crustaceans, plants and some vertebrates and there have been reports of the role of chitinase in the suppression of pathogens.

R. Mitchell and M. Alexander, "The Mucolytic Phenomenon and Biological Control of Fusarium in Soil", Nature, 190, 109–110 (1961) describes naturally occurring mucolytic, or fungi-lysing, soil bacteria (genera Bacillus and Pseudomonas) which suppress soil Fusarium by means of chitinase activity. B. Sneh, "Use of Rhizosphere Chitinolytic Bacteria for Biological Control", Phytopath. Z., 100, 251–56 (1981) discloses naturally occurring chitinolytic isolates identified as Arthrobacter sp. and Serratia liquifaciens. Sneh also discloses introduction of a chitinolytic bacterial strain from the genus Arthrobacter into the rhizosphere to protect carnation seedlings from Fusarium wilt.

A. H. Michael and P. E. Nelson, "Antagonistic effect of soil bacteria on Fusarium roseum culmorum", Phytopathology, 62, 1052–1056 (1972) discloses similar control with a naturally occurring Pseudomonas species.

J. Monreal and E. T. Reese, "The Chitinase of Serratia marcescens", Canadian Journal of Microbiology, 15, 689–696 (1969) describes a Serratia marcescens bacterial strain (QMB1466) selected as the most active chitinase producer out of a number of naturally occurring bacterial and fungal strains tested. Other strains tested which displayed some chitinase activity included bacterial strains from the genera Enterobacter and Streptomyces, and fungal strains from the genera Aspergillus, Penicillium and Trichoderma. Chitinase is characterized as an induced enzyme system in strain QMB1466, i.e., the yields of chitinase produced by the strain were higher when chitin was present. Monreal et al. reports at p. 692 that chitinase production on a chitin medium is repressed by the addition of other carbon-containing metabolites, e.g., sugars, to the medium. The Serratia marcescens enzyme system is described as extracellular and including endochitinase, a chitobiase and a "factor" for hydrolysis of "crystalline" chitin.

The naturally occurring *Serratia marcescens* chitinase system is further described in R. L. Roberts and E. Cabib, "*Serratia Marcescens* Chitinase: One-Step Purification and Use for the Determination of Chitin", *Analytical Biochemistry*, 127, 402–412 (1982).

J. D. Reid and D. M. Ogrydziak, "Chitinase-Overproducing Mutant of *Serratia marcescens*", *Applied and Environmental Microbiology*, 41, 664–669 (1981) describes work with a mutant of *Serratia marcescens*, strain IMR-IE1 obtained by mutation of strain QMB1466. The mutant had increased chitinase activity compared to strain QMB1466, as measured by zones of clearing on chitin-agar plates. On page 664 Reid et al. refers to the "high rate of reversion of IMR-1E1 to decreased levels of chitinase production."

C. I. Kado and P. F. Lurguin, "Prospectus for Genetic Engineering in Agriculture", *Phytopathogenic Prokaryotes*, Vol. 2, M. S. Mount and G. H. Lacy eds., 309 (1982), while not discussing the role of chitinase in controlling chitin-containing pathogens, notes the possibility of a different approach to controlling fungi, namely, inserting into bacteria genes coding for compounds which inhibit chitin synthase in fungi. That is, the compound chitin synthase, necessary for production of chitin in fungi, would be inhibited by the bacterial compounds.

P. M. Miller and D. C. Sands, "Effects of Hydrolytic Enzymes on Plant-parasitic Nematodes", *Journal of Nematology*, 9, 192–197 (1977) describes the effect of chitinase, obtained from a commercial supplier, on certain nematodes. Miller et al. discloses that chitinase hydrolytic enzymes are toxic to certain nematodes, in particular *Tylenchorhynchus dubius*, the toxicity being greater in aqueous solution than in soil.

There are a number of limiting factors and disadvantages with respect to work to date on biological control of plant pathogens using chitinase-producing bacteria introduced into the soil. First is the inability to regulate the production of chitinase in the introduced bacteria in such a way that proper amounts of chitinase are produced. Second is the limited ability of many of such bacteria to colonize and persist in the rhizosphere of host plants, a key consideration for effective biocontrol. Particularly important in this respect is the ability of biocontrol bacteria to colonize the roots of host plants effectively, the roots being the site of much plant-pathogen interaction. Third is that chitinase production is repressed in the presence of other carbon sources, e.g., metabolites released by the root. Another problem, at least as to mutants, is reversion to forms exhibiting decreased levels of chitinase production. There have been a number of reports of methods for introducing foreign DNA into plants. One approach is introduction by transformation using Agrobacterium, in particular *Agrobacterium tumefaciens*; M. Bevan et al., *Ann. Rev. Genet.*, 16, 357–384 (1982); L. Ream et al., *Science*, 218, 854–859 (1982). This introduction may be carried out by cocultivation of plant protoplasts with Agrobacterium, followed by plant regeneration; Marton et al., *Nature*, 277, 129–131 (1979); R. B. Horsch et al., *Science*, 223, 496–498 (1984). The introduction may also be carried out using binary vectors; A. Hoekema et al., *Nature*, 303, 179–180 (1983); P. van den Elzen et al., *Plant Mol. Biol.*, 5, 149–154 (1985); M. Bevan, *Nucl. Acids Res.*, 12, 8711–8721 (1984). Where the foreign DNA is from a non-plant source, the foreign DNA (structural gene, i.e., encoding sequence) may be fused to a plant promoter; L. Herrera-Estrella et al. *Nature*, 303, 209–213 (1983); R. T. Fraley et al., *Proc. Natl. Acad. Sci.*, 80, 4803–4807 (1983); J. T. Odell et al., *Nature*, 313, 810–812 (1985); J. Jones et al., *EMBO J.*, 4, 2411–2418 (1985).

SUMMARY OF THE INVENTION

The present invention generally relates to the cryoprotection of plants. In particular, a method is provided for protecting plants from freeze or chill damage, comprising transforming the plants with DNA which encodes chitinase. In a particular aspect, the method of the present invention comprises transforming plants with chitinase DNA, growing the plants in field conditions under which they are or may be subjected to chilling or freezing temperatures, and selecting or harvesting plants which display no or reduced chilling or freezing damage, or otherwise display an improved resistance to such damage.

In a related aspect, the present invention also provides a method of preparing a sweeter plant or fruit, in particular, an edible plant or fruit, comprising transforming the plant with DNA which encodes a chitinase. Fruit or plants of the invention may be selected which display enhanced levels of reducing sugars or sweetness. Such fruits or plants may additionally be selected for enhanced post-harvest storage life.

BRIEF DESCRIPTION OF THE DRAWINGS

FIGS. 1A–1C show the DNA sequence of a 2.3 kb DNA fragment from pCHIT1251, as determined by M13-dideoxynucleotide DNA sequencing (SEQ ID NO: 1). The predicted amino acid sequence of the chitinase A gene is given above the nucleotide sequence (SEQ ID NO: 2).

DESCRIPTION OF THE PREFERRED EMBODIMENTS

Figure 2:
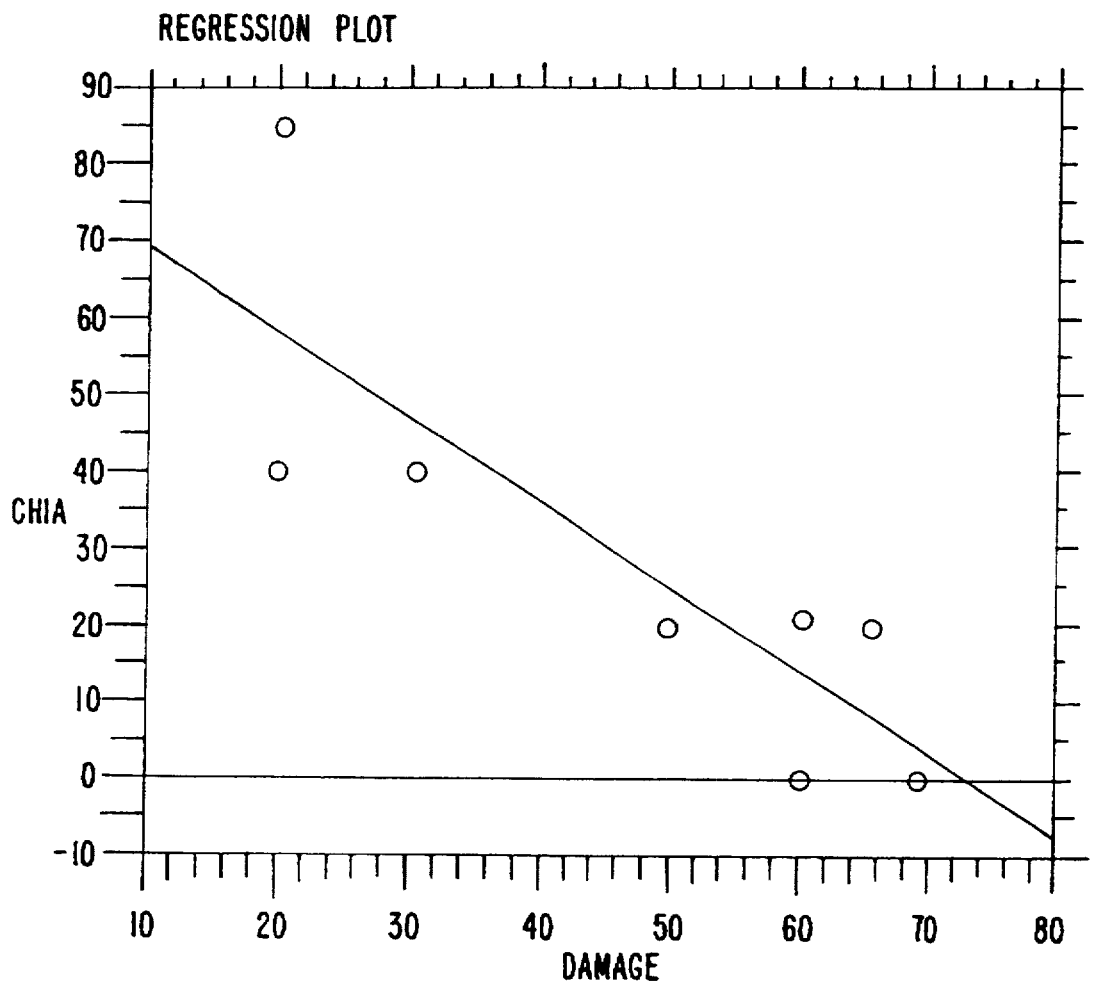
FIG. 2 is a graphical and tabular depiction of the regression line between ChiA activity and frost damage in cherry tomato transformants.

The present invention comprises novel man-made bacteria and plants, which have the ability to produce and secrete chitinase as the result of introduction of foreign DNA. The foreign DNA is isolated from a foreign source, bacterial or otherwise, or is substantially homologous to such DNA.

The term "substantial homology" refers to nucleotide sequences which share a majority of their sequence. Generally, this will be at least about 90% of their sequences and preferably about 95% of their sequence. Another indication that sequences are substantially homologous is if they hybridize under stringent conditions (see, e.g., Maniatis et al., *Molecular Cloning—A Laboratory Manual*, Cold Spring Harbor Laboratory, Cold Spring Harbor, N.Y., 1982. Stringent conditions will depend upon various parameters and will be different in different circumstances. Generally, stringent conditions are those in which the salt concentration is at least about 0.2 molar and the temperature is at least about 60° C.

The novel bacteria can be prepared using various means, including the use of appropriate vectors, for introducing the foreign DNA, and thus the capacity to produce chitinase, into a bacterial cell or a parent of a bacterial cell under conditions where chitinase activity is expressed. The vectors are used to clone and introduce the foreign DNA which encodes for chitinase activity. The novel bacteria can be used to introduce chitinase into the soil, particularly into the soil rhizosphere, thereby providing a means of inhibiting chitin-containing or chitinase-sensitive plant pathogens, including fungi and nematodes, and thereby also providing a means of enhancing the growth and well being of plants sensitive to such pathogens.

The present invention provides a means of overcoming limitations of the prior art methods of bacterial control of chitinase-sensitive plant pathogens. The invention provides a means of introducing sufficient chitinase production capacity into a strain. The invention also provides a means to introduce chitinase capacity into strains best suited to function in the soil and rhizosphere, in particular root colonizing rhizobacteria strains. Further, in accordance with the invention, the problem of reversion of modified strains to wild type is overcome in that the novel strains of the invention result from the actual introduction of genetic material, rather than from mutation. Additionally, the invention provides the means to overcome the problem of repression of chitinase activity in the presence of root exudates or other carbon sources, in that regulatory systems can be employed which render the bacterial cell insensitive to such repression.

The present invention further comprises a method of introducing into plants the ability to produce chitinase as the result of introduction into the plant of foreign DNA encoding for chitinase activity. Accordingly, the invention also comprises a method of inhibiting chitinous (chitin containing) plant pathogens by such introduction of foreign DNA under conditions whereby the plant produces (expresses) chitinase in active form. More particularly, plants may be protected against fungi, nematodes, insects and disease agents. As used herein, "in active form" means chemically active (capable of degrading chitin) or biologically active (capable of inhibiting chitinous plant pathogens). In addition, portions of the chitinase A gene encoding the signal sequence (i.e. the leader peptide that allows the protein to be secreted) can be linked to foreign DNA other than the chitinase A gene.

The foreign DNA to be introduced into the plant is isolated from a foreign source, in particular a bacterial source, or is substantially homologous to such DNA. The foreign DNA is introduced into the plant using plant transformation techniques, in particular using Agrobacterium procedures whereby the foreign chitinase DNA is first introduced into Agrobacterium in an appropriate vector, in accordance with the method of the invention, and then introduced into the plant by transformation with Agrobacterium. Such introduction into the plant is preferably carried out where the foreign DNA is fused to a plant promoter such that the foreign DNA (the structural gene) is under the transcriptional control of the plant promoter. Preferred sources of foreign chitinase DNA for plant transformation are ATCC accession numbers 39637 and ATCC 67152.

The present invention in addition comprises plants which have been rendered resistant to, or capable of inhibiting, chitinous plant pathogens by virtue of introduction of foreign chitinase encoding DNA into the plant under conditions whereby the transformed plant expresses chitinase in active form. The invention also comprises progeny of such transformed plants. As used herein "transformed plant" means a plant into which foreign DNA has been introduced. Any transformable plant may be transformed in accordance with the invention. The term "plant" as used herein includes whole plants, plant parts, seeds, plant cells, plant calli and plant tissue cultures. Preferred plants for transformation in accordance with the invention include tobacco, Brassica spp., soybean, sugarbeet, cotton, tomato (including cherry tomato), pepper, alfalfa, potato, wheat, barley, rice, corn, pea, carrot and other fruit and vegetable plants (in particular, solanaceous fruit-bearing plants).

The present invention also comprises methods for creating plants which are resistant to, or display increased resistance to, frost (freezing) damage or chilling damage. The invention further comprises plants upon which such resistance has been conferred as a result of introduction of foreign chitinase encoding DNA into the plant under conditions whereby the transformed plant expresses chitinase in active form. The invention also comprises progeny of such transformed plants.

In a related aspect, the present invention also provides a method of preparing a sweeter plant or fruit, in particular, an edible plant or fruit, comprising transforming the plant with DNA which encodes a chitinase. Fruit or plants of the invention may be selected which display enhanced levels of reducing sugars or sweetness. Such fruits or plants may additionally be selected for enhanced post-harvest storage life.

The novel bacterial cells of the invention are made by introduction of foreign DNA, or heterologous DNA, which codes for production of, or expression of, the enzyme chitinase. The term "chitinase" is used herein to mean chitin-degrading enzyme, the term "chitin-degrading" embracing both chitin-hydrolyzing and chitin-solubilizing. The term "chitinase DNA" is used herein to mean DNA which encodes for chitinase, and embraces foreign chitinase DNA obtained directly or indirectly from a source organism, including bacteria, fungi and plants, as well as DNA which regardless of source is substantially homologous to such foreign chitinase DNA. "Chitinase activity", or "chitinolytic activity", as used herein, means the ability or capacity of a bacterial cell to produce chitinase. Such chitinase can be secreted by the bacteria into the immediate environment.

Chitinase DNA can be obtained from a wide variety of naturally occurring bacteria which are known to or can be shown to produce chitinase, including bacteria from the genera Serratia, Bacillus, Pseudomonas, Arthrobacter, Enterobacter, and Streptomyces. Bacterial strains containing chitinase DNA have been known and available from laboratories or collections for years. For instance, chitinase-producing Serratia marcescens strain QMB1466, which was described by Monreal et al. in 1969 and by Reid et al. in 1981, (in each case the reported source of the strain being the U.S. Army Natick Laboratory Culture Collection) is available from a number of sources, including the American Type Culture Collection at Rockville, Md. (ATCC 990). Chitinase-containing bacterial strains are also readily obtainable by known techniques by virtue of their widespread distribution in nature. Such strains in general are found in soil, on plants, on insects and in water systems, as well as in other places where chitin is present. For example, chitinolytic bacteria can be isolated from the rhizosphere of a wide variety of plants including sugar beet, cotton, bean or carnation. Chitinase-producing bacteria can also be obtained from root surfaces, fungal resting structures (e.g., sclerotia, chlamydospores), nematode egg masses, insect or arthropod exo-skeleton and irrigation water.

Isolation of bacterial strains containing chitinase DNA can be accomplished by a number of techniques, including direct isolation on chitin containing media, enrichment or baiting with chitin or fungal hyphae. These techniques are common and known to those skilled in the art. Chitinase-producing fungi can be isolated from sources such as those stated above for chitinolytic bacteria, again using standard techniques for plating fungi. See, in general, J. Tuite, *Plant Pathological Methods: Fungi and Bacteria*, Burgess Publishing Co. (1969) with respect to techniques for isolation of bacteria and fungi.

Foreign chitinase DNA for conferring chitinase activity on a host or recipient bacterium can be obtained directly from a source organism, e.g., bacteria, fungi, yeast, insect or plant, using techniques of genome fragmentation and DNA isolation known to those skilled in the art. For instance, for a bacterial source organism, isolated as explained above, total bacterial DNA (that is, the entire genome including chromosomal DNA and extra-chromosomal DNA) is isolated by standard techniques, e.g., lysis of bacteria in the presence of appropriate detergents, proteases and chelating agents, followed by phenol and chloroform extractions and precipitation with ethanol. The isolated DNA is partially digested to various degrees with an appropriate restriction enzyme or enzymes selected on the basis of appropriate sites in the cloning vector which is to be used. The products of the digestion process are fractionated by standard techniques, for instance on a glycerol gradient. Fractions containing DNA in an appropriate size range, e.g., about 22 to about 32 kb (kilo bases), are selected for insertion into an appropriate vector using known techniques, for instance as described below, thus yielding a genomic library (consisting of cosmid clones, in the case of a cosmid vector).

An alternative to obtaining chitinase DNA directly by genome fragmentation of a source organism is obtaining chitinase DNA indirectly by isolating, from the source organism, messenger RNA (mRNA) corresponding to chitinase DNA. A cDNA (copy DNA) library can be prepared from the mRNA, using reverse transcriptase in accordance with techniques known to those skilled in the art, and inserted into an appropriate cDNA expression vector, such that clones encoding chitinase activity could be detected by clearing of chitin on plates.

The choice of particular vector turns on a number of considerations known to those skilled in the art, including the size of the fragment, nature of the host, number and position of restriction sites desired, and selection marker or markers desired. Techniques for introduction of DNA into a vector and subsequent introduction of the vector into the host bacteria are known to those skilled in the art. See in general T. Maniatis et al, "Molecular Cloning, a Laboratory Manual," Cold Spring Harbor Publications, 1982 (hereinafter Maniatis) with respect to techniques for insertion of DNA fragments into a host bacterium (as well as with respect to general techniques for fragmentation and fractionation of a genome.)

Introduction of foreign DNA into the host bacteria results in the creation of a bank of modified (i.e. transformed or transduced) host bacteria which can be screened for chitinase DNA. In many cases the host bacteria will be *E. coli*. The screening can be carried out by plating the host strains on a medium which contains chitin, e.g., colloidal chitin. The development of zones of clearing in the chitin around a colony is evidence that the colony is chitinolytic. Microscopic examination showing dissolution of surrounding chitin particles is further evidence. Alternative means to screen will be apparent to those skilled, e.g., plating on a fungal lawn, or chemical tests to show the presence of chitinase.

For those bacteria shown by screening to exhibit chitinase activity, there can be optionally employed a subsequent subcloning to reduce the quantity of cloned DNA which is not involved in the coding for chitinase. An appropriate enzyme digestion is carried out and the digestion products ligated to another more convenient cloning vector, e.g., one with high copy number, and the ligation products are again transformed into *E. coli* bacteria by known techniques. Transformants are screened for chitinase production as described above.

After the cloning and any subcloning, if desired, the chitinase DNA can be transferred from the first host (transferor or donor) bacterial cell into a second host (transferee or recipient) bacterial cell. This transfer can be accomplished using known techniques, for instance by conjugation using helper plasmids to mobilize the plasmid into the transconjugant cell, the specifics depending on the transferor bacterium, the recipient bacterium, and the cloning vector which is used to propagate the chitinase DNA. For instance, if the chitinase DNA is cloned on an IncP (incompatibility group P) type plasmid derivative, such as pLAFR1 transfer to a second host strain in many instances can be accomplished by conjugation, e.g., using a helper plasmid such as pRK2013. See in general G. Ditta et al, "Broad Host Range DNA cloning system for Gram-negative bacteria: Construction of a gene bank of *Rhizobium meliloti*, Proc. Acad. Sci., 77, 7347–7351 (1980) (hereinafter Ditta), with respect to conjugation using helper plasmids. Where the intended use of the bacteria modified to have chitinase ability is in control of plant pathogens residing in the soil, the bacteria of choice will normally be rhizobacteria. In that event chitinase DNA is transferred from the first host, normally *E. coli*, into the second host rhizobacterial strain.

Depending on the systems and circumstances involved in transferring a vector containing chitinase DNA from one bacterial cell to another, various techniques known to those skilled in the art may be used to ensure proper expression of the chitinase DNA in the host. For instance, an effective regulatory or promoter system will be necessary to bring about proper expression, that is, to ensure that the production of chitinase, encoded for by foreign chitinase DNA, can be brought about under conditions where chitinase production is desired. If the promoter from the source organism (i.e. the promoter which normally works in the source organism with the foreign chitinase DNA) is not effective in the host, it may be necessary to incorporate into the vector a regulatory system different from that which controlled the foreign DNA in the source organism. A promoter system of choice may be one which allows the bacterial cell to produce chitinase in a manner insensitive to the presence of carbon sources, e.g., root metabolites, in the immediate environment.

That is, the cell can be made to produce chitinase constitutively. Various other techniques to enhance chitinase activity in the modified cell may be employed as well, e.g., multicopy vectors or means to enhance secretion of the chitinase from the cell.

Plasmids containing chitinase DNA, i.e., clones or chimeric plasmids, can be introduced into a bacterial host by transformation, e.g., using $CaCl_2$, the transformed cell being called the transformant. The plasmid may be a cosmid vector containing chitinase DNA, i.e., a cosmid clone, and if so it can also be introduced into the bacterial cell by transduction, the product cell being the transductant.

The particular adaption of rhizobacterial cells to the rhizosphere is related to their ability to multiply and compete at the root-soil interface or the root surface, or in the intercortical cell spaces. Root colonizing rhizobacteria typically reach population densities of $10^4$ or greater colony forming units (cfu) per mg of root tissue, from low initial populations, during the first several weeks of plant growth. Various rhizobacteria have been described, including strains from the genera Pseudomonas (in particular *P. fluorescens* and *P. putida*), Agrobacterium, Enterobacter and Alcaligenes. See in general T. Suslow, "Role of Root-Colonizing Bacteria in Plant Growth", *Phytopathogenic Prokaryotes*, Vol. 1, M. S. Mount and G. H. Lacy eds., 187–223 (1982) for a discussion of root colonizing rhizosphere bacteria and their properties. The choice of root colonizing strain to receive chitinase DNA will turn on the plant to be protected, the pathogen or pathogens to be protected against, the method of application, and the cultural practices related to the crop of interest.

For bacterial strains which already have some chitinase activity, introduction of chitinase DNA in accordance with the present invention serves to enhance chitinase activity in the host. Other bacteria already have anti-fungal (fungicidal) or anti-nematodal (nematicidal) capacity by some mechanism other than chitinase activity, in which case introduction of chitinase DNA confers chitinase activity and enhances anti-pathogen ability.

The present invention can also be used in combination with the introduction of some other foreign DNA, that is foreign DNA other than chitinase DNA, into a bacteria or plant. For instance, in the case of rhizobacteria, such other foreign DNA could provide the host with some other form of anti-pathogen activity or with some other means to allow it to enhance the soil environment to the benefit of the plant. Another example is the introduction into a plant cell of a foreign gene attached to the nucleotide sequence encoding the signal peptide sequence of the chitinase A gene. Such foreign genes for introduction into a plant cell could be from a variety of sources (e.g., bacterial, plant, mammalian, yeast or fungal) and from a number of classes of genes, e.g., genes to protect plants against pathogens (including antifungal genes, e.g., cecropia, magainin, attacins or lysozymes); genes to protect plants against environmental stresses (such as antifreeze genes and salt tolerance genes); and genes to allow plant cells to produce desired pharmaceutical or other peptides, in particular where the peptide is to be overproduced for collection and purification (such as genes for growth hormones or insulin). The expressed polypeptide will then be released into the environment.

The present invention is of agricultural use as a means for the production of chitinase, including the production of chitinase as an antibiotic for the purpose of degrading or otherwise inhibiting, repelling or killing plant pathogens harmful to a wide variety of agricultural crops.

The invention has particular utility for inhibiting chitinase-sensitive fungi or nematodes (that is, fungi or nematodes which are inhibited, repelled or destroyed in the presence of chitinase), where such fungi or nematodes or their activities in soil or on plant surfaces are harmful to plants. Regardless of the mechanism by which such pathogens are injurious to plants, their inhibition serves to enhance plant growth and health.

The invention also has utility for providing cryoprotection to plants. Plants may be transformed with chitinase DNA (encoding either endochitinase or exochitinase) to protect the plants against chilling damage (0°–10° C.) or freezing/frost damage (below 0° C.). As exemplified in Example 5 herein concerning cherry tomato plants, plants so transformed have been found to display enhanced resistance with respect to plant frost damage, fruit frost damage for unharvested fruit, and frost damage for fruit harvested from plants which were subjected to field freezing or frost conditions. As demonstrated in Example 5, an inverse correlation was observed between chitinase activity in transformed plants and frost damage to plants in the field (Table V) and also between chitinase levels and frost damage to ripened fruit harvested from plants which were subjected to frost in the field (Table VIII). As also demonstrated in Example 5, the same plants displayed a direct correlation between levels of soluble reducing sugar (sucrose, glucose, fructose) and both chitinase activity (Table VI) and resistance to frost damage of unharvested fruit (Table VII). As further demonstrated in Example 5, harvested fruit of plants grown under non-freeze, non-chill conditions in the field displayed chilling resistance upon storage in the lab under chilling conditions (Table IX).

Chitinase is known to degrade chitin into soluble sugar units (e.g., N-acetyl-glucosamine monomers or small oligomers of same); Roberts et al., "Plant and Bacterial Chitinases Differ in Antifungal Activity," (1988) *J. Gen. Microbiol.* 134, 169–176. Small soluble compounds, in particular sugars, are known to be associated with or causative of protection against chilling or freezing damage; see Finkle, B. J. et al., "Cryoprotective Compounds into Viable Freezing of Plant Tissues," in *Cryopreservation of Plant Cells and Organs* (Chapter 5), Pages 75–113, CRC Press, Inc. Boca Raton, Fla. (1985); Sakai, et al., "The Role of Sugar and Related Compounds in Variations of Freezing Resistance," (1968) *Cryobiol.* 5(3), 160–174. Without being bound to any particular mechanism or theory, it is believed that the cryoprotection conferred on plants by the method of the invention may be the result of, or associated with, degradation by chitinase of plant polysaccharides (e.g., cleavage of beta-1,4 glycosidic bonds in the polysaccharide components of the cell wall such as hemicellulose and pectin) to yield increased levels of soluble sugars (monomers or small oligomers) which in turn results in enhanced protection against freezing or chilling damage.

The method of the invention may be used to achieve a result of protection against freezing or chilling with plant transformants both where chitinase is produced in a form where it remains within the cell and also where chitinase is produced in combination with a signal or transit sequence which transports the chitinase into extra-cellular spaces. A preferred form of signal sequence is the DNA signal sequence from a gene encoding chitinase A, which sequence is capable of directing secretion of a polypeptide (in this case chitinase) from a plant cell.

Accordingly, the method of the invention may be used to confer resistance or protection against freezing (frost) or chilling damage (collectively, cold damage or "cryodamage") for any plants (including dicots and monocots and including fruits and other plant parts of such plants) which may be transformed with chitinase DNA in accordance with the transformation techniques taught herein and known in the art. Protection to fruits includes protection exhibited post-ripening. The method thus comprises transforming plants with chitinase DNA, growing the plants in field conditions under which they are or may be subjected to chilling temperatures (0°–10° C.) or freezing temperatures (below 0° C.), and selecting or harvesting the plants (or their fruit) which display no or reduced chilling or freezing damage or which otherwise display resistance or increased resistance to chilling or freezing damage. Given the enhanced levels of soluble reducing sugars, the method of the invention also may be used to create sweeter plants and fruits with associated flavor attributes for edible plants, fruits, and other plant parts. The method of the invention may be further used to confer other properties on plants associated with reducing sugars content or elevated reducing sugars content, including improved storage, preservation and shelf-life properties. The method thus further comprises transforming plants with chitinase DNA and selecting plants with enhanced sweetness or enhanced storage properties. Plants with enhanced sweetness may be selected by selecting for enhanced levels of reducing sugars or enhanced levels of soluble sugars. Preferred reducing sugar levels are at least 2.5%, with at least 3% being more preferable.

Bacteria, and particularly rhizobacteria, modified in accordance with the present invention and grown to sufficient proportions, e.g., by fermentation, can be used to combat chitin-containing soil pathogens by application of the bacteria to soil, seeds, vegetative plant parts or irrigation water. For example, mucolytic bacteria created in accordance with the invention can be used in such ways to attack or inhibit fungi. The modified bacteria can be applied in various formulations containing agronomically acceptable adjuvants or carriers in dosages and concentrations chosen to maximize the beneficial effect of the rhizobacteria.

For application to soil, to soil mixes, or to artificial plant growth media, the modified bacteria may be applied as a powder or granule in a suitable carrier. Alternatively, the modified bacteria may be applied as a suspension or dispersion, e.g., as an aqueous suspension with a suitable protectant such as methylcellulose, dextran, dextrin, alginate, magnesium silicate. The modified bacteria may also be applied as a wettable powder.

For application to seeds, the modified bacteria may be applied as part of a seed coating composition, for instance mixed with xanthan gum, magnesium silicate, methylcellulose, gum arabic, polyvinyl pyrollidone, dextrins or dextrans. In addition, small amounts of partially hydrolyzed chitin may be added to the pelleting mix, dust granule, suspension, or wettable powder to enhance chitinase production. See in general T. Suslow et al., "Rhizobacteria of sugar beets: effects of seed application and root colonization on yield", *Phytopathology*, 72, 199–206 (1982); and, J. Kloepper et al., "Development of a powder formulation for inoculation of potato seed pieces", *Phytopathology*, 71, 590–592 (1981), for a discussion of rhizobacteria and seed coating compositions, both of which are incorporated herein by reference.

Bacteria into which chitinase capability has been introduced by this invention may also be applied to the above-ground surface of a plant, e.g., the leaf or stem surface, either to permit the modified bacteria to travel or spread to the roots or to inhibit chitinase-sensitive pathogens which may be present on blossoms or plant surfaces, for instance, fungal pathogens such as Botrytis, Monilinia, Alternaria, and Cercospora. Blossoms of Prunus sp., in particular, provide an ideal environment for the growth of epiphytic bacteria, e.g., *Pseudomonas syringae* or *Erwinia herbicola*, that have the ability to produce inhibitory levels of chitinase. Similar results can be obtained by introducing chitinase-producing capacity directly into the plant.

The method of the invention can also be used for introduction of chitinase genes into species of Rhizobium which enter into a nitrogen fixing symbiosis within the nodules of leguminous plants. The nodules are frequently the point of entry of pathogenic fungi and nematodes.

The method of the invention additionally provides a means to introduce chitinase DNA into a bacterium, e.g., Agrobacterium, which is used to transfer the foreign DNA to plants. Other known means of transforming plants are also available to transfer chitinase or other foreign DNA to plants and the invention is not limited to any given method of transformation. Such transfer results in a direct means for the plant to inhibit chitinase-sensitive plant pathogens, either alone or in conjunction with bacteria modified to have chitinase ability. A particularly attractive form of such transfer is one where the chitinase DNA is expressed by the plant only at the site of pathogen attack, e.g., only in the root cells.

Both of the above applications (introduction of chitinase activity into Rhizobium or plants) would involve subcloning the chitinase genes and bringing them under the control of different regulatory sequences from those which act in the source organism. For example, elevated expression in *E. coli* could be brought about by using the lac z system (B-galactosidase structural gene promoter). In nodules elicited by Rhizobium a nitrogenase promoter could be used, and in plant leaves the promoter of a highly expressed leaf gene could be used. Any of a number of such plant promoters can be used in accordance with the invention. As used herein, the term "plant promoter" means a promoter, whether of plant source or otherwise, which can function in a plant, i.e., which can control or regulate the transcription of a structural gene within a plant cell. As used herein, the term "promoter" means a DNA sequence which can control the level of transcription of a downstream DNA sequence which corresponds to a structural gene (encoding region). Plant promoters may be fused to structural genes by cutting and ligating of DNA sequences, together with substitution of specific nucleotide(s) as needed in ways known in the art. The following plant promoters, preferred for use in regulating chitinase DNA in plants, have been fused to chitinase DNA and introduced into plants resulting in chitinase production by the plants, in accordance with the invention: nopaline synthase promoter (from *Agrobacterium tumefaciens*) chlorophyll a/b binding protein promoter; ribulose bisphosphate carboxylase small subunit promoter; and cauliflower mosaic virus 35S promoter.

Plants transformed with chitinase DNA may be characterized or subjected to assays in various ways. The presence of messenger RNA corresponding to chitinase DNA may be assayed in known ways (e.g., Northern hybridization, primer extension assay) as a measure of transcription of the introduced DNA. The presence of chitinase protein may be assayed in known ways (e.g., SDS-PAGE) as a measure of translation. Chitinase produced by the plant may be assayed for chemical activity by measuring the capacity of chitinase produced by the plant to hydrolyze chitin. The biological activity of the chitinase may be assayed by various bioassays which can be used to determine the effect of chitinase produced by the plant on chitinous plant pathogens. One such bioassay is described in Example 4(f).

EXAMPLES

1. Introduction of Chitinase DNA into *E. Coli*.

The overall procedure was to construct a set of random cosmid clones from the *Serratia marcescens* genome which would cover the entire genome several times over in such a way that statistically there was at least a 99% chance of covering every DNA sequence in the genome. Clones carrying an entire chitinase gene were inserted in *E. coli*, which is quite closely related, taxonomically, to *S. marcescens*. The work involved in isolating clones which carry chitinase DNA had the following steps, as explained in detail below.

a) Isolating total *S. marcescens* DNA.

b) Partial digesting of *S. marcescens* DNA.

c) Purifying a fraction of the partial DNA digest in which the DNA fragment size was 22 kb–32 kb.

d) Ligating the purified DNA to a cosmid cloning vector.

e) In vitro packaging into lambda phage.

f) Transfecting *E. coli* cells with lambda phage and selection.

g) Carrying out small scale plasmid isolations on tetracycline resistant colonies and digesting to check that foreign DNA had been cloned.

h) Plating and screening for colonies which clear chitin.

i) Characterizing cosmid clones conferring chitinase activity.

(a) Isolation of Total *S. marcescens* DNA

Cells of *Serratia marcescens* QMB1466 were removed from culture storage and streaked on agar media to form single isolated pure colonies.

A single colony was inoculated into 5 mls of 1-bactotryptone, 0.5% yeast extract and 0.5% NaCl (hereinafter LB) liquid medium and grown overnight with shaking at 28° C. One ml aliquots were spun down in 1.5 ml Eppendorf tubes and resuspended in 0.3 ml 20 mM Tris, 10 mM EDTA (pH 8.0). 0.1 ml of 5% SARKOSYL and 0.1 ml of 5 mg/ml pronase were added and the cells were incubated at 37° C. for lysis to proceed for two hours. After this incubation, the solution was passed through a 19 gauge needle to shear the DNA slightly and thus to reduce the viscosity of the solution. Next, 0.5 ml of phenol (pH adjusted to 8.0 with Tris) was added and the mixture shaken in the Eppendorf tube prior to centrifugation. This step was repeated three times, with the supernatant from one centrifugation being re-extracted with fresh phenol. Then the supernatant was extracted three times with 0.8 ml of a one-to-one mixture of phenol and chloroform/isoamyl alcohol (24:1) and once with 0.8 ml of chloroform/isoamyl alcohol. The supernatant from this final spin was brought to 0.3M sodium acetate and the DNA precipitated by addition of 2.5 volumes of ethanol. After centrifugation to pellet the DNA precipitate, the DNA was redissolved in 0.1 ml of 10 mM Tris/1 mM EDTA (hereinafter TE) An aliquot was taken and diluted into 0.5 ml for measurement of the optical density at 260 nm in order to find out the concentration of nucleic acid. Typically this procedure permitted the isolation' of 100–200 micrograms of DNA.

(b) Partial Digestion of Isolated DNA

The procedure adopted for establishment of appropriate DNA to enzyme ratios for correct partial digestion was the widely used method described in Maniatis pp. 282–283. The objective was to establish conditions where the maximum fluorescence of the partial digestion products occurred in the size range 40–50 kb. 10 ug (microgram) of DNA was incubated in 150 ul (microliter) of the restriction enzyme buffer specified by the manufacturer (New England Biolabs) and dispensed in 15 ul aliquots except for one tube which contained a 30 ul aliquot. 10 units of EcoRI were added to the 30 ul aliquot, the contents of the tube were mixed and a 15 ul aliquot withdrawn, added to the next tube and the contents mixed, and the procedure repeated down the series of tubes. After a one hour incubation at 37° C. the reaction was terminated with 3 ul of 0.25M EDTA/50% glycerol/ 0.01% bromophenol blue, and the digestion products run on a 0.4% agarose gel which was stained with 0.5 ug/ml ethidium bromide and examined by fluorescence in short wave uv light. The migration of the partial digestion products in the gel was compared to size markers of known size. Once conditions were established for partial digestion of chromosomal DNA to the appropriate degree, 200 ug of DNA was digested to this degree in an appropriately scaled-up volume. Partial digests giving weight average sizes at the maximum fluorescence position of 40 kb and 20 kb were mixed and fractionated on a glycerol gradient.

(c) Fractionation of Partial Digestion Products by Differential Sedimentation

The digestion was terminated by addition of enough 0.5M EDTA to bring the final EDTA concentration to 10 mM followed by incubation of the reaction at 65° C. for 10 minutes, and then was kept on ice until the gradient was loaded. An aliquot was checked for the degree of digestion being appropriate by running on a 0.3% agarose gel with DNA fragment size markers of appropriate size (e.g., digests of lambda DNA).

Linear gradients of 10–40% glycerol were prepared in 38 ml polyallomer tubes. The 10% or 40% glycerol stock solutions were made up in 1M sodium acetate, 5 mM EDTA. 0.5–1.5 ml aliquots of partial digests containing 100–300 ug of partial digest were loaded on top of the gradients which were then spun at 25000 rpm for 16 hours.

At the end of the centrifugation the tubes were punctured at the bottom, 1 ml aliquots were dripped out and the DNA in them analyzed by agarose gel electrophoresis in 0.3% gels. Fractions containing DNA in the size range 22–32 kb were chosen for further work.

Fractions of this size range were pooled and dialyzed against 10 mM Tris 1, mM EDTA (pH 8.0) for 24 hours with three buffer changes.

These fractions were then concentrated by isobutanol extraction (Maniatis, p. 463) to about 0.3 ml, brought to 0.3M sodium acetate and the DNA was precipitated by addition of 2.5 volumes of ethanol. The precipitated DNA was redissolved in 10 μl of TE and the quantity of DNA recovered estimated by measuring the optical density at 260 nm of a dilution of an aliquot of this DNA.

(d) Ligation of Size-fractionated DNA to Vector DNA

The vector used for cloning the Serratia DNA was pLAFR1. As described by A. Friedman et al., "Construction of a broad host range cosmid cloning vector and its use in the genetic analysis of *Rhizobium meliloti*", *Gene*, 18, 289–96 (1982), pLAFR1 has a single Eco RI site, a cos site from lambda phage for in vitro packaging, and a tetracycline resistance marker. The vector pLAFR1 selects DNA inserts of about 22 to about 32 kb in length. The vector can be mobilized to other genera of bacteria where it can replicate.

5 ug of pLAFR1 DNA was digested to completion with EcoRI, and the DNA phenol extracted and ethanol precipitated. The precipitated DNA was redissolved in 20 ul of TE.

Test ligations were carried out on both the pLAFR1 DNA and the size-fractionated DNA which was to be cloned to verify that the ends were ligatable.

In a typical ligation of pLAFR1 DNA to size-fractionated Serratia DNA, a 5-fold molar excess of Serratia DNA was adopted. A typical ligation contained in 10 ul 0.4 ug of pLAFR1 DNA and 3 ug of Serratia DNA. The reaction was 66 mM Tris (pH 7.5), 10 mM MgCl2, 1 mM ATP, 15 mM dithiothreitol, 0.05% BSA, 0.5 mM spermidine and 20 units/ul T4 DNA ligase (New England Biolabs) The reaction was carried out overnight at 15° C.

(e) In Vitro Packaging of Ligation Products into Lambda Phage Particles

Packaging extracts were prepared as described in Maniatis p. 264–267. Freeze thaw lysate was frozen at −80° C. in 10 ul aliquots, and sonic extract was frozen away in 15 ul aliquots. One tube of each was thawed on ice and the freeze thaw was added to the sonic extract and mixed gently. Then 5 ul of the ligation was added to the mixture and after gentle mixing, the packaging reaction was allowed to proceed at 25° C. for one hour. The reaction was diluted with 500 μl of 10 mM MgCl2 10 mM Tris (pH 7.5), 10 mM NaCl (hereinafter SM), and 500 ul chloroform were added. The mixture was inverted five times in the capped Eppendorf tube and spun for five minutes in an Eppendorf bench centrifuge.

(f) Transfection of *E. coli* Cells with Packaged Cosmid Clones

*E. coli* strain DH1 (ATCC #33849) displays no detectable chitinase activity (see Table II) The strain was grown to saturation in LB containing 0.4% maltose. A 0.2 ml aliquot was withdrawn and mixed with 0.1 ml of SM and 10 ul of the diluted packaging mix. After mixing gently, phage absorption was allowed to proceed for 20 minutes at 37° C.

The transfection was added to 1.7 ml of LB in a tube and the cells permitted to grow out for 40 minutes at 37° C. In the first experiment 20, 100, 500, and 1100 ul aliquots were plated on LB plates containing 1.5% agar and 10 mg/l tetracycline to investigate the colony forming units derived from the packaging. The plates were incubated at 37° C. for 16–20 hours. In a typical experiment a 10 ul aliquot of packaging dilution would contain 1000 colony forming units.

(g) Small Scale Plasmid Preps to Investigate the Quality of the Bank

Single tetracycline resistant colonies were picked from plates at the end of stage (f) above into 8 ml aliquots of LB containing 0.5 g/l uridine and incubated with aeration for 12–20 hours at 37° C. Cells were spun down and resuspended in 0.2 ml 50 mM glucose, 20 mM Tris, 10 mM EDTA (pH 8.0). The cells were then lysed in 0.4 ml 0.2M NaOH, 1% SDS. This was neutralized with 0.3 ml 3M potassium acetate which had been brought to pH 5.0 with acetic acid and incubated on ice for five minutes. After thorough mixing, the mixture was spun at 8000 rpm for ten minutes. The supernatant was precipitated with 0.6 volumes of isopropanol and the DNA recovered by centrifugation in a bench top Eppendorf centrifuge. The pelleted DNA was redissolved in 0.3 ml TE and extracted with equal volumes of phenol and chloroform. After centrifugation the supernatant was brought to 0.3M sodium acetate and the DNA precipitated with 2.5 volumes of ethanol. After centrifugation the DNA was redissolved in 0.05 ml of TE and 5 ul aliquots were used for restriction enzyme digestion followed by gel electrophoresis.

In a typical experiment eight independent clones were grown up and 50% of them contained inserts.

(h) Direct Plating on Chitin-containing Medium for a Screen for Chitinase Activity Theoretically about 500 independent clones of a genome the size of *E. coli* should give a 99% chance of getting any particular sequence among the clones. It is desirable to independently isolate any clone with chitinase activity at least once. Five thousand colonies were plated out at about 250 colonies per plate on LB medium containing 2.0% colloidal chitin and 10 mg/l tetracycline. This concentration of chitin had been previously shown to clearly evidence the chitinase activity of *S. marcescens* QMB1466.

After about seven days at 32° C., certain colonies gave rise to clear zones around them. Altogether about twenty different colonies gave rise to convincing clear zones in their vicinity. See Table II and step (i) below. In Table II, DH1 is the original *E. coli* (step f); DH1/pLAFR1 is *E. coli* DH1 containing the cosmid vector pLAFR1 but without insert; DH1/C3 is *E. coli* DH1 containing cosmid vector pLAFR1 with one chitinase size class insert; and DH1/C12 is *E. coli* DH1 containing cosmid vector pLAFR1 with a second chitinase size class insert (this strain has been deposited with the American Type Culture Collection in Rockville, Md. as ATCC No. 67152).

(i) Characterization of Cosmid Clones Conferring Chitinase Activity

Ten of the twenty colonies were inoculated into 8 ml of LB tet medium and plasmid DNA prepared as above. This DNA was analyzed for the DNA sequences in the plasmid by digestion with EcoRl. Each of the ten plasmid DNAs fell into one of two distinct size classes after EcoRl digestion. Seven out of the ten cosmid clones showed one large EcoRl fragment of about 25 kb, in addition to the vector band of 21.6 kb. Of these, one (C3) was chosen for further characterization (see Table II and associated text) Three of the plasmids showed insert fragments of 3 kb, 9.5 kb and 17 kb, in addition to the vector band of 21.6 kb. Of these, one (C12) was chosen for further characterization (see Table II and associated text).

The phenotype of chitinase production was shown to be plasmid borne by reintroduction of the plasmid into *E. coli* bacteria by transformation of the bacteria with plasmid DNA. 1 ul out of the 50 ul of plasmid DNA prepared as in (h) was incubated with 0.1 ml of competent *E. coli* cells prepared essentially by the method of M. Dagert and S. D. Ehrlich, *Gene*, 6, 23–28 (1979). After a 20 minute incubation on ice and a two minute heat shock at 37° C., bacteria were grown out in LB medium for one hour and plated on LB tetracycline chitin plates. Bacteria which acquired tetracycline resistance all acquired the capacity to make chitinase.

The above experiments provide evidence that *S. marcescens* QMB1466 contains two independent chitinase genes which have been isolated on distinct cosmid clones. The means is therefore presented to express these genes either together or separately in a recipient organism.

2. Introduction of Chitinase DNA into Pseudomonas Species.

(a) Isolation of Pseudomonas Species from the Rizosphere

*Pseudomonas fluorescens* strain NZ130 and *Pseudomonas nutida* strain MK280 were isolated from radish roots, and soybean roots, respectively, by plating on King's Medium B from serial dilutions of root washings. See in general T. Suslow, "Role of Root-Colonizing Bacteria in Plant Growth," *Phytopathogenic Prokaryates*, Vol. I, M. S. Mount and G. H. Lacy eds., 187–223 (1982) for details of fluorescent Pseudomonas isolation and characterization for colonizing ability and plant growth promotion. Strain NZ130 has been identified as *P. fluorescens* Biotype D (*Pseudomonas chlororaphis* in some taxonomies) and strain MK280 as *P. putida*. Their characteristics include the following:

TABLE I

|  | NZ130 | MK280 |
|---|---|---|
| Fluorescent on King's Medium B | + | + |
| Fluorescent on King's Medium A | − | − |
| Pyocyanine Production | − | − |
| Oxidase | + | + |
| Lecithinase | + | − |
| Gelatin Hydrolysis | + | − |
| Arginine Dihydrolase | + | + |
| Growth at 4° C. | + | − |
| Growth at 37° C. | − | + |
| Growth at 41° C. | − | − |
| Green Phenazine Pigment | + | − |
| Motility | + | + |
| Inhibition of Erwinia sp | + | + |
| Inhibition of Pythium sp. | + | − |
| Clones resistant to rifampicin (100 ug/ml) | + | + |

Strain NZ130 has plant growth promoting characteristics on a number of crops including potato, radish, soybean, cotton, and sugar beet. Strain NZ130 also has biological control characteristics with respect to Pythium sp., but no measurable chitinase activity. Root colonization data collected for NZ130, in general, reach average population densities of $5.5 \times 10^4$ colony-forming units (cfu) per mg root tissue (dry weight) on radish, soybean and cotton.

Strain MK280 has been shown to increase the emergence of soybean and to effectively colonize roots of soybean and sugar beets. Population densities, in general reach as high as $1.2 \times 10^6$ cfu/mg root tissue.

(b) Mobilization of Cosmid Clones into Pseudomonas Species pLAFR1 is a mobilizable cloning vector derived from pRK290 (Ditta). It can be mobilized into other genera of bacteria using a helper plasmid pRK2013 in a three-way mating process. Two Pseudomonas strains were chosen as recipients for these matings; these were NZ13Or (NZ130, rifampicin resistant) and MK28Or (MK280, rifampicin resistant). The donor (transferor) strain was *E. coli* DH1 or HB101 containing one of the two chitinase cosmid clones, and the helper strain was HB101 containing pRK2013, all of which materials are commonly available.

Donor, recipient and helper strains were grown up to mid-log phase, without selection, in LB. 0.05 ml aliquots from each strain were added to each other and the mixture put out as a 0.15 ml aliquot on an LB plate for 12–16 hours at room temperature. After the conjugation, a loop was run through the cells. Cells from the loop were resuspended in 10 mM $MgSO_4$, and the mixture of cells plated at various dilutions on minimal sucrose tetracycline (10 mg/l) plates.

This procedure selected against *E. coli*, which cannot grow on minimal sucrose plates, and selects for Pseudomonas cells which acquire the tetracycline resistance gene. Exconjugant cells were obtained and were tested for chitinase activity as above. See Table II. In Table II, TSO31 is NZ13Or with cosmid vector pLAFR1 but without insert; TSO43 is NZ13Or with cosmid vector pLAFR1 with one chitinase size class insert (corresponding to the insert of DH1/C12 present in ATCC No. 67152) TSO35 is MK28Or with cosmid vector pLAFR1 but without insert; and TSO44 is MK28Or with cosmid vector pLAFR1 with one chitinase size class insert (corresponding to the insert of DH1/C3). TSO44 has been deposited with the American Type Culture Collection in Rockville, Md. (ATCC No. 39637). Note that Table II also lists data for two naturally occurring, chitinase-producing strains which are not root colonizers: *Serratia marcescens* strain ATCC 990 and a strain of naturally occurring Arthrobacter sp.

TABLE II

Efficiency of Chitin Hydrolysis by Chitinase-Producing Bacteria*

| STRAIN | Growth Temperature | | | | |
|---|---|---|---|---|---|
| | 21° C. | 25° C. | 28° C. | 32° C. | 37° C. |
| *Serratia marcescens* | | | | | |
| ATCC 990 | 1.28 | 1.51 | 2.17 | 2.22 | 1.41 |
| Arthrobacter sp. | | | | | |
| TS037 | 1.0 | 1.06 | 1.07 | 2.0 | 1.0 |
| *E. coli* | | | | | |
| DH1 | 1.0 | 1.0 | 1.0 | 1.0 | 1.0 |
| DH1/pLAFR1 | 1.0 | 1.0 | 1.0 | 1.0 | 1.0 |
| DH1/C3 | 1.12 | 1.12 | 1.12 | 1.13 | 1.13 |
| DH1/C1 | 2.12 | 1.12 | 1.12 | 1.32 | 1.82 |
| *P. fluorescens* | | | | | |
| TS031 | 1.0 | 1.0 | 1.0 | 1.0 | 1.0 |
| TS043 | 1.10 | 1.10 | 1.10 | 1.28 | 1.14 |

TABLE II-continued

Efficiency of Chitin Hydrolysis by Chitinase-Producing Bacteria*

| STRAIN | Growth Temperature | | | | |
|---|---|---|---|---|---|
| | 21° C. | 25° C. | 28° C. | 32° C. | 37° C. |
| *P. putida* | | | | | |
| T5035 | 1.0 | 1.0 | 1.0 | 1.0 | 1.0 |
| TS044 | 1.12 | 1.06 | 1.06 | 1.14 | 1.15 |

*Efficiency reported as the ratio of clearing zone diameter in LB agar amended with 2.0% colloidal chitin to colony diameter. A value of 1.0 represents no clearing detectable.

3. Introduction of Chitinase DNA in Tobacco Under Control of a Nopaline Synthase Promoter.

(a) Plant Transformation.

The coding region of the chitinase gene in the C12 chitinase size class insert (described in Example 2 above) was determined by nucleotide sequence analysis of the DNA (this coding region referred to herein as the chiA gene). The sequence of the chitinase A gene is presented in FIGS. 1A–1C (SEQ ID NO: 1 and SEQ ID NO: 2). Comparison of the N-terminal sequence with signal sequences of other prokaryotes (See, for example, Inouye et al. (1983), *Science*, 221, 59–61) reveals the putative chitinase signal peptide. As can be seen, the eighth through eighteenth amino acids are hydrophobic and the predicted cleavage site is between the alanines at the 23 and 24 positions. See, J. Jones et al., *EMBO J.*, 5, 463–473 (1986) regarding sequence information and G. Van Heijne *EMBO J.*, 3, 2315–2318 (1984) regarding signal peptide sequences, both of which are incorporated herein by reference. This nucleotide sequence information was used in the creation of constructions which led to the expression of the bacterial chitinase gene in plant cells. Sequence information of use in practicing the invention is set forth in the paragraphs below.

These constructions required the modification of nucleotide sequences at the 5' end of the chitinase gene. This was carried out in several steps. An NdeI site (CATATG) was introduced at the N-terminal methionine-encoding ATG of the chiA gene by oligonucleotide site-directed mutagenesis; M. J. Zoller et al., *Nucleic Acid Res.*, 10, 6487–6500 (1985). Sequence information is given below.

```
chiA wild type sequence  GGAATCAGTT  ATGCGC(SEQ ID NO:3)
chiA wild type sequence  GGAATCAGTT  ATGCGC(SEQ ID NO:3)
chiA mutated sequence    GGAATCACAT  ATGCGC(SEQ ID NO:4)
                         (gives an NdeI site at the ATG)
```

The chiA gene was cut with NdeI and fused to a DNA fragment carrying the Agrobacterium nopaline synthase (nos) promoter which had also been modified in a similar manner to yield an NdeI site at the ATG. The nopaline synthase gene has been characterized; Depicker et al., *J. Mol. Appl. Genet.*, 1, 561–573 (1982). Using these two constructions, the chiA gene was litigated directly to the nos promoter. Sequence information is shown below.

```
nos-chiA fusion  TCTGCAT  ATGCGCAAA(SEQ ID NO:5)
```

Modifications of the resulting fusion were made using site-directed mutagenesis in order to improve the translation signals. Sequence information is shown below.

modified nos/chiA fusion #1  TCTGAAT ATGCGCAAA(SEQ ID NO:6)
modified nos-chiA fusion #2  TCTGAAT ATGGCCAAA(SEQ ID NO:7)

Each of these constructions was set up with a nos gene fragment carrying signals for polyadenylation placed at an EcoRV site 25 bp past the TAA. These constructions were introduced into plant cells using Agrobacterium by ligating them into binary vectors, P. van den Elzen et al., *Plant Molecular Biology*, 5, 149–154 (1985) and mobilizing the resulting constructions into the Agrobacterium strain LBA4404, A. Hoekema et al., *Nature*, 303, 179–180 (1983).

These strains were then used in cocultivation experiments with tobacco cells, and calli which grew on kanamycin were selected.

(b) Assays

Large numbers of independent calli (approximately 400) prepared as described above were harvested approximately six weeks after initiating the selection regime and were analyzed for the expression of mRNA homologous to the bacterial chitinase gene and for protein which was antigenic to an antibody raised against the bacterial chitinase protein. This antibody was prepared using a protein sample in which the chitinase band had been eluted from a preparative acrylamide gel and injected into rabbits to elicit antibodies to the protein in the rabbit serum. J. Jones et al., *EMBO J.*, 5, 467–473 (1986).

The results of these experiments can be summarized as follows:

(i) Chimeric nos-chitinase mRNA was detected in the transformed plant cells. About two-fold more mRNA was detected in modification #2 than in modification #1 or in the original CATATG construction.

(ii) Bacterial chitinase protein was detected in the plant cells. The modified nos-chiA fusion #2 gave rise to about four-fold more protein on a per total protein basis than modification #1 and eight-fold more than the original NdeI site fusion.

In short, these results showed the expression of chitinase protein in plant cells in detectable quantities.

4. Introduction of Chitinase DNA in Tobacco Under Control of a Chlorophyll A/B Binding Protein Promoter (CAB Promoter) or a Ribulose Bisphosphate Carboxylase Small Subunit Promoter (SSU Promoter).

(a) Preparation of CAB Constructs

The modified nos-chiA fusion #2 of Example 3 generated a BalI restriction site (TGGCCA) immediately downstream of the ATG. This was used to form a fusion with a chlorophyll a/b binding protein gene (CAB 22L) octopine synthase fusion which also contained a BalI restriction site in a corresponding position relative to the ATG. See P. Dunsmuir et al., *Nucleic Acid Res.*, 13, 2503–2518 (1985). This construction had the DNA sequence shown below.

CAB 22L/ocs  AAACC ATGGCCAGATCCCGGG(SEQ ID NO:8)

DNA carrying this construction was cut with BalI and ligated to BalI cut nos/chiA modification #2 in such a way that the nos 3' polyadenylation signals were retained 3' to the chiA gene. The resulting construction had a sequence around the ATG as shown below.

CAB-chiA fusion  AAACC ATGGCCAAA(SEQ ID NO:9)

(b) Preparation of SSU Constructs

The resulting CAB-chiA fusion described above retained an NcoI (CCATGG) site at the ATG. This was used to fuse the chiA coding region to the 5' end of an expression cassette which used 5' and 3' sequences from a gene highly expressed in the petunia leaf, namely SSU gene #301; see C. Dean et al., *EMBO J.*, 4, 3055–3061, (1985). This expression cassette (pAGS007) contains a coding sequence flanked by an NcoI site at the ATG and a BglII (AGATCT) BamHI (GGATCC) or BclI (TGATCA) site close to and 3' to the termination codon to be placed between SSU301 5' and 3' sequences. The expression cassette is deposited within *E. coli* JM83-AMB007 (ATCC 67125); see U.S. patent application Ser. No. 883,604, which is incorporated by reference. Fusion to the SSU cassette creates a novel sequence in the vicinity of the chitinase ATG. Sequence information is given below.

SSU-chiA fusion  TAACC ATGGCCAAA(SEQ ID NO:10)

During the construction of the nos-chiA fusion the chiA coding region fused to the nos 5' sequences was cloned as a BamHI (Klenow treated) to EcoRV (partial digestion) fragment into the SmaI site of a pUC vector containing a TaqI fragment which encodes the nos 3' region. The EcoRV site used was 25 bp downstream of the chiA translation termination codon. This fusion therefore added the nos 3' region onto the 3' end of the chiA coding region, completing the nos-chiA fusion. The resulting plasmid had a BamHI site (from the pUC linker) at the junction of the chiA and nos 3' sequences. This BamHI site was used to fuse the 3' flanking sequences of the SSU expression cassette to the chiA coding sequence (a BamHI site can fuse to a BglII site).

(c) Plant Transformation

The CAB and SSU constructions were cloned into the BamHI site of binary vector pAGS135 which is very similar to pAGS112 described in P. van den Elzen et al., *Plant Molec. Bio.*, 5, 149–154 (1985). The difference is that the unique XhoI site in pAGS112 has been removed by Klenow+dNTP treatment of the linearized DNA and religation. The resulting constructions were mobilized into Agrobacterium strain LBA4404. A. Hoekema et al., *Nature*, 303, 179–180 (1983).

The resultant Agrobacterium strains were cocultivated with protoplasts isolated from *N. tabacum*. P. van den Elzen et al., *Plant Molec. Bio.*, 5, 149–154 (1985). Transformed plant material was selected for its ability to grow on 50 mg/l kanamycin, then regenerated.

The transgenic tobacco plants were transferred to the greenhouse once they had established a sufficient root system. They were assayed for expression of chitinase RNA and chitinase protein three weeks after they had been in the greenhouse (previously established to be the time of maximal CAB and SSU RNA levels).

(d) Assay for Chitinase Protein

The level of chitinase protein was assayed by a Western blot analysis in which an antibody probe was used to detect chitinase protein on a nitrocellulose filter carrying the size-fractionated polypeptides. The amount of chitinase protein was evaluated using a standard dilution series of chitinase protein isolated from bacterial strains which abundantly express the chitinase. These experiments showed that in the most abundantly expressing SSU-chitinase transformants, the bacterial chitinase protein accumulated to 0.1–0.2% of total leaf protein. Of fifteen plants assayed, seven gave rise to greater than or equal to 0.1% of total protein as chitinase. For the CAB-chitinase transformant, one gave rise to a protein level of 0.1% chitinase, and on average these constructions gave rise to 2–4 fold less chitinase protein than was found in the SSU-chitinase transformants.

(e) Assay for Chitinase mRNA

The levels of chitinase RNA were assayed by primer extension. In this assay an oligonucleotide specific to the chitinase RNA was annealed to total RNA and then extended in a reverse transcriptase reaction back to the 5' end of the message. The amount of extended fragment then gave a measure of the levels of chitinase RNA in the total RNA. The results correlated broadly with the levels of chitinase protein observed in the individual transformants. A comparison of the chitinase RNA levels from plants transformed with noschiA, CAB-chiA and SSU-chiA showed that the highest expressing SSU-chiA construct transformant gave rise to about 15× more chitinase mRNA than the best CAB-chitinase constructs and at least 200× more mRNA than the nos-chitinase constructs.

(f) Assay for Chitinase Biological Activity

Biological activity of chitinase produced by transformants was assessed in a bioassay using, as a model disease, Tobacco Brown Spot caused by *Alternaria alternata* and *Alternaria lonaipes*. The pathogen infects leaves causing discrete, readily quantified lesions and is of a class of fungi, Fungi Imperfecti, having cell walls containing chitin.

Leaf disks, 9.0 cm in diameter, were cut from the center of tobacco leaves taken from acropetal positions 4–10 as described by H. Spurr, *Tobacco Science*, 17, 145–148 (1973). Plants utilized were either transformed with a CAB:chiA fusion, 1771.2, or were transformed but did not contain chiA, SBT2.9. The parental tobacco plant, Wis38, had previously been tested for susceptibility to Brown Spot and ATCC strain 26293 of *A. lonaipes* was most virulent. Conidial suspensions were prepared as described (H. Spurr, *Tobacco Science*, 17, 145–148, 1973), and adjusted to approximately $\log_{10}$ 5.0 conidia ml$^{-1}$ in a chamber haemocytometer. Twelve drops (each of 10 ul) of conidial suspension were placed in a uniform pattern on the underside of each of seven leaf disks per treatment. Leaf disks were incubated in a Conviron Seed Germinator with settings at 21° C., 95% RH, and 8 hour low intensity fluorescent light photoperiod.

After eight days, leaf disks were observed for comparative disease development. Total necrotic lesions were counted and the lesion diameter measured with a metric caliper. Diameter values given (Table III) are inclusive only of the brown necrotic tissue and not the chlorotic halo associated with the whole infection. Leaf disks from identical leaf positions were most directly comparable as differences in susceptibility with leaf age were known.

Wis38 plants containing and expressing chiA had fewer total Brown Spot lesions, fewer lesions per disk, and necrotic areas which did develop were of generally lesser diameter than plants not transformed with chiA.

TABLE III

| Plant | Total Lesions | Lesions/ disk | a Diam./Total | b Diam./Leaf |
|---|---|---|---|---|
| 1771.2 | 10 | 1.7 | 0.2 | 1.1 |
| SBT2.9 | 23 | 3.3 | 0.6 | 1.5 | a Mean diameter of necrotic lesions for all inoculated spots.
b Mean diameter of necrotic lesions for most susceptible leaf pairs.

In another series of readings, three other transformants (1781.1, 1781.5, 1781.4) prepared as above, were compared with a control (Wis38). The results, shown in Table IV below, again show the positive effect of chitinase, produced by the transformed plant, on disease resistance. Each of the three transformants showed, relative to the control, decreased infection ratio and decreased lesion sizes.

TABLE IV

| | Relative level of x̄ infection | | X̄ diam./ | |
|---|---|---|---|---|
| Plant | chiA | ratio (%)$^a$ | X̄ diam./lesion/ disk (mm)$^b$ | lesion (mm)$^c$ |
| Wis38 | 0 | 82 | 6.4 ± 0.4 | 6.4 ± 0.20 |
| 1781.1 | IX | 43 | 6.1 ± 0.5 | 6.2 ± 0.33 |
| 1781.5 | 5X | 62 | 5.6 ± 0.8 | 6.3 ± 0.38 |
| 1781.4 | 20X | 55 | 4.8 ± 0.4 | 4.6 ± 0.33 |

$^a$Mean percent infection (infections/total inoculation points X100) per replication.
$^b$Mean infection lesion (necrotic area) diameter per leaf disk replication.
$^c$Mean infection diameter normalized per necrotic lesion.

5. Protection of Cherry Tomato Plants Against Freezing or Chilling Damage a. Plant Transformation All manipulations were carried out under sterile conditions. Experiments were carried out in parallel using a culture of Agrobacterium LBA4404 containing the gene for ChiA (an exochitinase) either in plasmid pPRSSChiA-GM which contains the signal sequence of the PR1b protein in substitution for the ChiA signal sequence region, or in plasmid pChiA; see, Lund et al., "A Plant Signal Sequence Enhances the Secretion of Bacterial ChiA in Transgenic Tobacco," (1992) *Plant Mol. Biol.* 18, 47–53; and, Howie et al., "Transgenic Tobacco Plants Which Express the chiA Gene From *Serratia marcescens* have Enhanced Tolerence to *Rhizoctonia solani*," (1994) *Transgenic Research* 3, 90–98. The culture was grown for 24 hours in minimal A medium at 28° C. Explants were excised from the midsections of 7–8 day old cotyledons of sterilely grown Baxters Early Bush cherry tomato (*L. esculentum*) seedlings on germination medium. The Agrobacterium culture was diluted in liquid 2% glucose-Oms (Murashige, T. et al. (1962), *Physiol. Plant* 15, 473–497) to a final concentration of 5×10$^5$/ml.

The explants were submerged in the Agrobacterium suspension for 20–30 minutes and then placed on cocultivation plates for 2 days at 25° C. The cocultivation was terminated by washing the leaf discs in liquid 2% glucose-Oms for 2 hours. The explants were then placed on solid regeneration media and cultured under high light fluence with an 8 hour dark period at 25° C. After 10 days kanamycin (250 µg/ml) resistant callus appeared and then small shoot buds by 3 weeks. At 5 weeks the healthy calli and shoots were transferred to fresh kanamycin selection regeneration (250 μg/ml) medium and within 2 weeks many transformed shoots emerged. The shoots were then excised and transferred to selective rooting medium. Plants that successfully developed shoots in this medium in 6–10 days were transferred to non-selective rooting medium for 2 weeks to check for residual Agrobacterium, and transplanted to soil.

For transformations with pChiA, the ChiA protein is expressed within the cell (15300 series transformants). For transformations with pPRSSChiA-GM the ChiA protein is secreted into the extracellular space (15400 series transformants). As explained below, the transformed plants were measured for ChiA activity; ChiA protein levels; reducing sugar levels; freezing (frost) damage; chill damage; and disease resistance.

b. Screening and Planting

The primary transformants were screened to determine the levels of expression of ChiA activity using the standard fluorimetric assay (Yang, et al., (1971) *J. Biochem.* 87, 1003–1014) for ChiA, as described in Howie et al., "Transgenic Tobacco Plants Which Express the chiA Gene From *Serratia marcescens* have Enhanced Tolerence to *Rhizoctonia solani*," (1994) *Transgenic Research* 3, 90–98. Subsequently the primary transformants were self-pollinated, the seed arising from these crosses was germinated and progeny plants were screened with kanamycin (250 μg/ml) in order to identify segregants which carry the ChiA gene which is linked to the kanamycin resistance marker. Plots of 35–40 progeny plants from each of seven independent transgenic tomato lines, together with Baxters Early Bush control plants (BEBC), were planted at an experimental farm and then assayed at the mature plant stage for ChiA activity, frost/chill damage, and fungal disease symptoms; and in fruit for ChiA activity, fungal disease symptoms, frost/chill tolerance, chill tolerance and reducing sugar levels.

c. Reducing Sugar Assay

The assay steps were as follows (see Nelson, et al., (1994) *J. Biol. Chem.* 153, 375–380): pool independent tomato fruit to reach 150 grams and then blend fruit for 30 second intervals in a blender to make a slurry; dilute the slurry 1000-fold with distilled water; aliquot the diluted slurry into 1 ml samples, add 1 ml of copper reagent, and then heat in boiling water for 11 min; cool in an ice bath, then add 1 ml Nelsons reagent and allow the tubes to stand for 30 min.; dilute the reaction with 7 ml $H_2O$ and read absorbance at 565 nm. By using the slope of the line from a standard curve, the % sugars in the sample was calculated.

d. Frost/Chill Damage Measurements

The plants growing in the field were visually rated for frost/chill damage (referred to as frost damage in Tables V–VIII) after a series of frosts. An estimate was made of the % of the total biomass for the 35–40 plants in the plot which exhibited frost/chill damage. The field grown fruit were rated for frost/chill damage by counting the number of fruits which were damaged and those which were not damaged after a series of frosts and chilling episodes.

In addition to the measurements of frost/chill damage in the field, fruit were also harvested after frost/chill episodes, at the mature green stage. The fruit were then ripened and rated for frost/chill damage and fungal disease which arises as a consequence of the damage incurred by freezing.

In order to establish the protection effect against chilling damage alone (as opposed to the combined effects of freezing and chilling which plants in the field experience as a consequence of being subjected to freezing conditions), measurements were made of fruit which had not been subjected to freezing or chilling temperatures in the field but which were stored post-harvest at chilling temperatures (4° C.).

e. Results

The results are shown in Tables V–IX, as explained below.

TABLE V

| Lines | ChiA Activity Equivalent ng/μg protein | % of Plants Exhibiting Frost Damage |
|---|---|---|
| BEBC | 0 | 70 |
| 15322 | 0 | 60 |
| 15328 | 19 | 65 |
| 15415 | 19 | 50 |
| 15326 | 20 | 60 |
| 15417 | 40 | 20 |
| 15426 | 40 | 30 |
| 15414 | 80 | 30 |

Table V shows ChiA activity compared to plant frost damage. Specifically, Table V lists the level of ChiA activity measured in the leaf and/or fruit tissue for each of 7 transgenic lines and BEBC (control). The percent of these exhibiting foliar frost damage in the field is listed. There is an inverse correlation between the extent of frost damage to the plants and the level of ChiA activity. FIG. 2 illustrates the regression line between ChiA activity and frost damage.

TABLE VI

| Lines | ChiA Activity Equivalent ng/μg protein | % Reducing Sugar |
|---|---|---|
| BEBC | 0 | 2.3 |
| 15322 | 0 | 2.9 |
| 15328 | 19 | 2.56 |
| 15415 | 19 | 2.9 |
| 15326 | 20 | 2.79 |
| 15426 | 40 | 2.44 |
| 15417 | 40 | 3.2 |
| 15414 | 80 | 2.93 |

Table VI shows sugar content compared to ChiA activity. Specifically, Table VI summarizes the measured reducing sugars levels together with ChiA activity levels in the transgenic lines and BEBC. Fruits were harvested at two distinct times (spaced by two weeks). The sugar levels in all of the transgenic lines were higher than the BEBC controls.

TABLE VII

| Lines | % Reducing Sugar | Field Frost Damage of Fruit |
|---|---|---|
| BEBC | 2.3 | 2.5 |
| 15426 | 2.44 | 3.5 |
| 15328 | 2.56 | 2 |
| 15326 | 2.79 | 3 |
| 15322 | 2.9 | 2 |
| 15415 | 2.9 | 3.5 |
| 15414 | 2.93 | 4 |
| 15417 | 3.2 | 4 |

Table VII shows sugar content of fruit compared to freezing damage of unharvested fruit in the field. There is a correlation between the elevated reducing sugar levels and increased resistance of the fruit to frost damage in the field. Field freezing ratings are on the same 1–5 scale as described below with respect to Table VIII and frost damage.

TABLE VIII

Frost damage and post harvest evaluation of chitinase expressing lines

| Lines | Chitinase Expression Level | Frost Damage | Disease Severity |
|---|---|---|---|
| B15417 | high | 4.6** | 5.0** |
| B15414 | high | 3.3** | 4.8** |
| B15322 | very low | 2.8 | 4.1* |
| BEBC | none | 2.5 | 3.2 |

Table VIII shows chitinase levels compared to post-harvest freezing and disease damage to fruit. Specifically, Table VIII summarizes data which describes ChiA levels and frost damage exhibited after ripening, and disease severity after ripening for fruit of 3 selected lines. Mature green fruit were collected from field plants that had been subjected to 5–7 frosts. Fruit were collected which exhibited no frost damage. Fruit were ripened at 20° C. and with 120 ppm ethylene in the lab for 7 days, and then immediately scored for frost damage. Frost severity ratings are from 1–5 and made at the red ripe stage, where 1 equals severe damage and 5 equals no damage. Disease severity ratings are from 1–5 and made at the red ripe stage, where 1 equals fruit which is completely necrotic and 5 equals fruit which shows no disease. The single asterisk (*) and double asterisk (**) denote significant difference from the control at P=0.05 and 0.001, respectively. Each value is the mean of 3 replications with 15–20 fruit per replication.

TABLE IX

Effect of Chilling on Lines Displaying Chitinase Activity.

| Chilling Treatment | Fruit Stage | Lines | % Chilling Damage |
|---|---|---|---|
| 15° C. | Breaker | 15414 | 5 |
|  |  | 15426 | 2 |
|  |  | BEBC | 2.5 |
|  | Light Red | 15414 | 2 |
|  |  | 15426 | 4.5 |
| 4° C. | Breaker | BEBC | 0 |
|  |  | 15414 | 42** |
|  |  | 15426 | 22** |
|  | Light Red | BEBC | 90 |
|  |  | 15414 | 11** |
|  |  | 15426 | 13** |
|  |  | BEBC | 46 |

Table IX shows chilling damage, for lines displaying chitinase activity (see Tables V and VI), under the following conditions. Tomato fruit were harvested at the mature green\breaker stage (referred to as Breaker in Table IX) or light red stage from fields which had not experienced any chilling or freezing conditions. The fruit were transported to the laboratory where they were incubated at 4° C. (a temperature known to induce chilling damage in unripe fruits) or 15° C. for two weeks. The fruit at 15° C. proceeded to the red ripe stage during that period, and were rated for damage at the end of storage. The fruit which were chilled were subsequently ripened by exposure to ethylene at 120 ppm at 20° C. for 6 days, and rated for chilling damage at the red ripe stage.

The data of Table IX illustrate that BEBC fruit at mature green/breaker stage were extremely sensitive to storage at 4° C. (90% damage). BEBC fruit at light red stage were less sensitive, but still suffered considerable damage (40% damage). Lines expressing ChiA activity were significantly less damaged by the chilling exposure both at the mature green/breaker stage (50–75% reduction in damage) and at the light red stage (75% damage reduction). In Table IX, percent chilling is the percentage of fruit showing chilling damage. Each value is the mean of 2 replications and each replication has 15 to 20 fruit. Means comparisons were made using the ANOVA and Fisher's PLSD test. The double asterisk (**) denotes significant difference as compared to the BEBC control at a given chilling treatment.

---

What is claimed is:

1. A method of producing a bacterial cell capable of producing chitinase, the method comprising transforming said bacterial cell with a nucleic acid encoding said chitinase which nucleic acid was isolated from a heterologous source, and whereby said bacterial cell is capable of expressing said nucleic acid.

2. The method of claim 1, wherein said bacterial cell is Pseudomonas.

3. The method of claim 2, wherein said bacterial cell is *Pseudomonas putida* strain #TS044 (ATCC No. 39637).

4. The method of claim 1, wherein said heterologous nucleic acid is isolated from *Serratia marcescens*.

5. A method of protecting a plant from chitinase sensitive plant pathogens, comprising:

transforming a bacteria with a nucleic acid encoding a chitinase which nucleic acid was isolated from a heterologous source; and growing said plant in the presence of an effective concentration of said bacteria.

6. The method of claim 5, wherein said bacteria is Pseudomonas.

7. The method of claim 6, wherein said bacteria is *Pseudomonas putida* strain #TS044 (ATCC No. 39637).

8. The method of claim 5, wherein said heterologous nucleic acid is isolated from *Serratia marcescens*.

9. The method of claim 5, wherein said chitinase sensitive plant pathogens are soil fungi.

10. The method of claim 5, wherein said chitinase sensitive plant pathogens are soil nematodes.

11. A plant seed-coating composition, said composition comprising an effective concentration of bacteria transformed with a nucleic acid encoding a chitinase, which nucleic acid was isolated from a heterologous source, whereby said bacteria is capable of expressing said nucleic acid, said composition further comprising an agronomically acceptable carrier.

12. The composition of claim 5, wherein said bacteria is Pseudomonas.

13. The composition of claim 6, wherein said bacteria is *Pseudomonas putida* strain #TS044 (ATCC No. 39637).

14. The composition of claim 5, wherein said heterologous nucleic acid is isolated from *Serratia marcescens*.

15. A soil composition capable of inhibiting chitinase sensitive plant pathogens, said soil composition comprising an effective concentration of bacteria transformed with a nucleic acid encoding a chitinase, which nucleic acid was isolated from a heterologous source, whereby said bacteria is capable of expressing said nucleic acid.

16. The composition of claim 15, wherein said bacteria is Pseudomonas.

17. The composition of claim 16, wherein said bacteria is *Pseudomonas putida* strain #TS044 (ATCC No. 39637).

18. The composition of claim 15, wherein said heterologous nucleic acid is isolated from *Serratia marcescens*.

19. The composition of claim 15, wherein said chitinase sensitive plant pathogens are soil fungi.

20. The composition of claim 15, wherein said chitinase sensitive plant pathogens are soil nematodes.

21. A bacterial cell having chitinase activity, said bacterial cell comprising a heterologous nucleic acid encoding said chitinase activity, whereby said bacterial cell expresses said nucleic acid, said bacterial cell being selected from the group consisting of Pseudomonas sp., *E. coli* and Erwinia sp.

22. An essentially pure nucleic acid sequence, said nucleic acid sequence being isolated from a source organism and which nucleic acid sequence comprises a segment that encodes for chitinase activity or is substantially homologous to a nucleic acid sequence isolated from a source organism and encoding for chitinase activity.

* * * * *